(12) United States Patent
Ishii et al.

(10) Patent No.: US 7,368,609 B2
(45) Date of Patent: May 6, 2008

(54) OPTICALLY ACTIVE 1-(FLUORO-, TRIFLUOROMETHYL- OR TRIFLUOROMETHOXY- SUBSTITUTED PHENYL)ALKYLAMINE N-MONOALKYL DERIVATIVES AND PROCESS FOR PRODUCING SAME

(75) Inventors: Akihiro Ishii, Saitama (JP); Masatomi Kanai, Saitama (JP); Yokusu Kuriyama, Saitama (JP); Manabu Yasumoto, Saitama (JP); Kenjin Inomiya, Saitama (JP); Takashi Ootsuka, Saitama (JP); Koji Ueda, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 11/705,089

(22) Filed: Feb. 12, 2007

(65) Prior Publication Data
US 2007/0142670 A1 Jun. 21, 2007

Related U.S. Application Data

(62) Division of application No. 10/476,650, filed as application No. PCT/JP03/11341 on Sep. 5, 2003, now Pat. No. 7,186,865.

(30) Foreign Application Priority Data
Sep. 6, 2002 (JP) ............................... 2002-261148

(51) Int. Cl.
C07C 211/00 (2006.01)
(52) U.S. Cl. ...................................... 564/384; 564/304
(58) Field of Classification Search .................... None
See application file for complete search history.

(56) References Cited

U.S. PATENT DOCUMENTS

2002/0103400 A1 8/2002 Ishii et al.
2003/0028021 A1 2/2003 Alvaro et al.
2004/0210817 A1 10/2004 Kapoor et al.

FOREIGN PATENT DOCUMENTS

WO WO 01/25219 A2 4/2001
WO WO 02/32867 A1 4/2002

OTHER PUBLICATIONS

G.H. Posner et al., " Methyl and n-Alkyl Ketones form Carboxylic Acid Chlorides and Organocopper Reagents" Tetrahedron Letters, No. 53, (1970) pp. 4647-4650, Great Britain.
Chemical Journal of Chinese Universities, Feb. 9, 1988, vol. 9, No. 2, pp. 134-139.
A. Gilbert, et al., "Excited State Substitution and Addition Reactions of Aryl Fluorides with Aliphatic Amines," Department of Chemistry, University of Reading, Jul. 1980, pp. 1393-1399.

Japanese Office Action dated Jun. 16, 2006 and an English translation thereof (Eight (8) pages).
Correspondence dated Jul. 28, 2006 (Two (2) pages).

Primary Examiner—Samuel Barts
(74) Attorney, Agent, or Firm—Crowell & Moring LLP

(57) ABSTRACT

An optically active 1-(fluoro-, trifluoromethyl- or trifluoromethoxy-substituted phenyl)alkylamine N-monoalkyl derivative represented by the formula 4 is produced by a process including (a) reacting an optically active secondary amine, represented by the formula 1, with an alkylation agent $R^2$—X, in the presence of a base, thereby converting the secondary amine into an optically active tertiary amine represented by the formula 3; and (b) subjecting the tertiary amine to a hydrogenolysis, thereby producing the N-monoalkyl derivative,

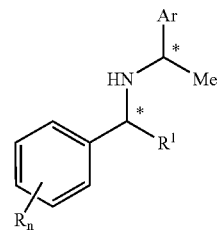

[1]

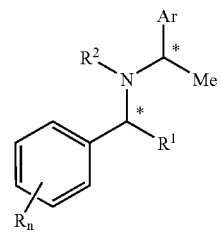

[3]

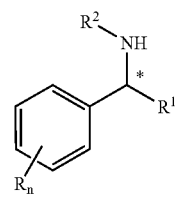

[4]

wherein R represents a fluorine atom, trifluoromethyl group or trifluoromethoxy group, n represents an integer of from 1 to 5, each of $R^1$ and $R^2$ independently represents an alkyl group having a carbon atom number of from 1 to 6, Me represents a methyl group, Ar represents a phenyl group or 1- or 2-naphthyl group, * represents a chiral carbon, and X represents a leaving group.

13 Claims, No Drawings

OPTICALLY ACTIVE 1-(FLUORO-, TRIFLUOROMETHYL- OR TRIFLUOROMETHOXY- SUBSTITUTED PHENYL)ALKYLAMINE N-MONOALKYL DERIVATIVES AND PROCESS FOR PRODUCING SAME

CROSS REFERENCE TO RELATED APPLICATIONS

This application is a division of application no. 10/476,650, filed Nov. 4, 2003 now U.S. Pat. No. 7,186,865, which was the U.S. national stage of international application no. PCT/JP03/11341, filed Sep. 5, 2003, the entire disclosure of which is incorporated herein by reference. Priority is claimed based on Japanese patent application no. JP 2002-261148, filed Sep. 6, 2002.

BACKGROUND OF THE INVENTION

The present invention relates to (a) optically active 1-(fluoro-, trifluoromethyl-, or trifluoromethoxy-substituted phenyl)alkylamine N-monoalkyl derivatives, which are important intermediates for medicines and agricultural chemicals, (b) processes for producing those derivatives, and (c) intermediates, which are obtained in the processes.

Of the above-mentioned N-monoalkyl derivatives, only optically active 1-(3,5-bis(trifluoromethyl)phenyl)ethylamine N-monomethyl is described in International Publication WO 01/25219, corresponding to U.S. Patent Application Publication 2003/0028021 A1, and International Publication WO 02/32867. In fact, WO 01/25219 or U.S. Patent Application Publication 2003/0028021 A1 discloses a process for producing optically active 1-(3,5-bis(trifluoromethyl)phenyl)ethylamine N-monomethyl by an optical resolution of a racemic mixture of 1-(3,5-bis(trifluoromethyl)phenyl)ethylamine N-monomethyl using malic acid.

SUMMARY OF THE INVENTION

It is an object of the present invention to provide a process for producing optically active 1-(fluoro-, trifluoromethyl-, or trifluoromethoxy-substituted phenyl)alkylamine N-monoalkyl derivatives.

It is another object of the present invention to provide novel compounds belonging to such N-monoalkyl derivatives.

It is still another object of the present invention to provide novel compounds, which are intermediates obtained in the process.

According to the present invention, there is provided a process for producing an optically active 1-(fluoro-, trifluoromethyl- or trifluoromethoxy-substituted phenyl)alkylamine N-monoalkyl derivative represented by the formula 4. This process comprises the steps of:

(a) reacting an optically active secondary amine, represented by the formula 1, with an alkylation agent represented by the formula 2, in the presence of a base, thereby converting the secondary amine into an optically active tertiary amine represented by the formula 3; and (b) subjecting the tertiary amine to a hydrogenolysis, thereby producing the N-monoalkyl derivative,

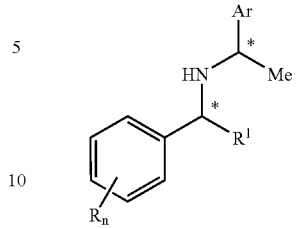

[1]

wherein R represents a fluorine atom, trifluoromethyl group or trifluoromethoxy group, n represents an integer of from 1 to 5, $R^1$ represents an alkyl group having a carbon atom number of from 1 to 6, Me represents a methyl group, Ar represents a phenyl group or 1- or 2-naphthyl group, and

* represents a chiral carbon, $$R^2—X \quad [2]$$

wherein $R^2$ represents an alkyl group having a carbon atom number of from 1 to 6, and X represents a leaving group,

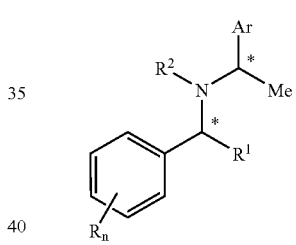

[3]

wherein R, n, $R^1$, Me, Ar, and * are defined as in the formula 1, and $R^2$ is defined as in the formula 2,

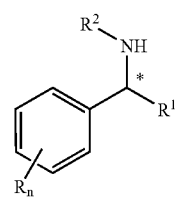

[4]

wherein R, n, $R^1$, and * are defined as in the formula 1, and $R^2$ is defined as in the formula 2.

According to the present invention, the secondary amine of the above step (a) may be produced by a process including the steps of:

(c) reacting a fluoro-, trifluoromethyl- or trifluoromethoxy-substituted phenyl alkyl ketone, represented by the formula 5, with an optically active primary amine represented by the formula 6 under an acidic condition to achieve dehydration and condensation, thereby producing an optically active imine represented by the formula 7; and (d) asymmetrically reducing the imine by a hydride reducing agent into the secondary amine,

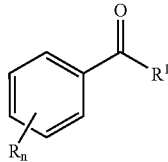

[5]

wherein R, n and $R^1$ are defined as in the formula 1,

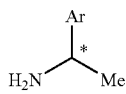

[6]

wherein Me, Ar and * are defined as in the formula 1,

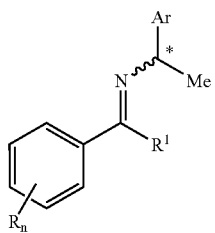

[7]

wherein R, n, $R^1$, Me, Ar and * are defined as in the formula 1, and a wave line in the formula 7 indicates that the imine is in an E configuration or Z configuration.

According to the present invention, there is provided a novel compound that is the above tertiary amine represented by the formula 3, which is the product of the step (a).

According to the present invention, there is provided another novel compound that is an optically active 1-(fluoro-substituted phenyl)alkylamine N-monoalkyl derivative represented by the formula 8,

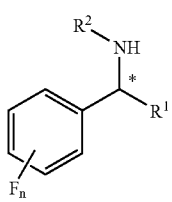

[8]

wherein n, $R^1$ and * are defined as in the formula 1, and $R^2$ is defined as in the formula 2.

According to the present invention, there is provided still another novel compound that is an optically active 1-(trifluoromethyl-substituted phenyl)alkylamine N-monoalkyl derivative represented by the formula 9,

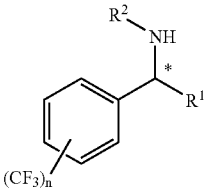

[9]

wherein n, $R^1$ and * are defined as in the formula 1, $R^2$ is defined as in the formula 2, and the N-monoalkyl derivative of the formula 9 is a compound except optically active 1-(3,5-bis(trifluoromethyl)phenyl)ethylamine N-monomethyl.

According to the present invention, there is provided a further novel compound that is an optically active 1-(trifluoromethoxy-substituted phenyl)alkylamine N-monoalkyl derivative represented by the formula 10,

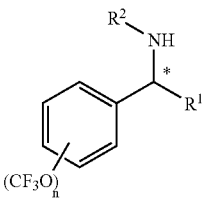

[10]

wherein n, $R^1$ and * are defined as in the formula 1, and $R^2$ is defined as in the formula 2.

The above novel N-monoalkyl derivatives represented by the formulas 8, 9 and 10 correspond to the N-monoalkyl derivative represented by the formula 4, which is the product of the step (b).

DESCRIPTION OF THE PREFERRED EMBODIMENTS

The inventors unexpectedly found that it is possible to efficiently produce the target compound, that is, an optically active 1-(fluoro-, trifluoromethyl- or trifluoromethoxy-substituted phenyl) alkylamine N-monoalkyl derivative (represented by the formula 4) with high optical purity and high yield by conducting the above process comprising the steps (a) and (b). Specifically, we unexpectedly found that the hydrogenolysis of the step (b) proceeds selectively on the side of the chiral auxiliary group to sever the N—C* bond only at the broken line "b" in an optically active tertiary amine represented by the following formula 11 (corresponding to the tertiary amine of the formula 3), although the tertiary amine has two similar α-arylalkyl groups positioned about the nitrogen atom.

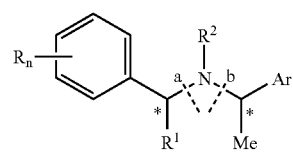

[11]

wherein R, n, $R^1$, Me, Ar, and * are defined as in the formula 1, and $R^2$ is defined as in the formula 2. Therefore, it is possible by the step (b) to selectively produce only the target product (i.e., the N-monoalkyl derivative represented by the formula 4).

Furthermore, according to the present invention, the raw material of the step (a), that is, the optically active secondary amine represented by the formula 1, can be produced by the above process comprising the steps of (c) and (d). In other words, the target product of the present invention can be produced by a process comprising the sequential steps of (c), (d), (a) and (b), as shown by the following reaction scheme.

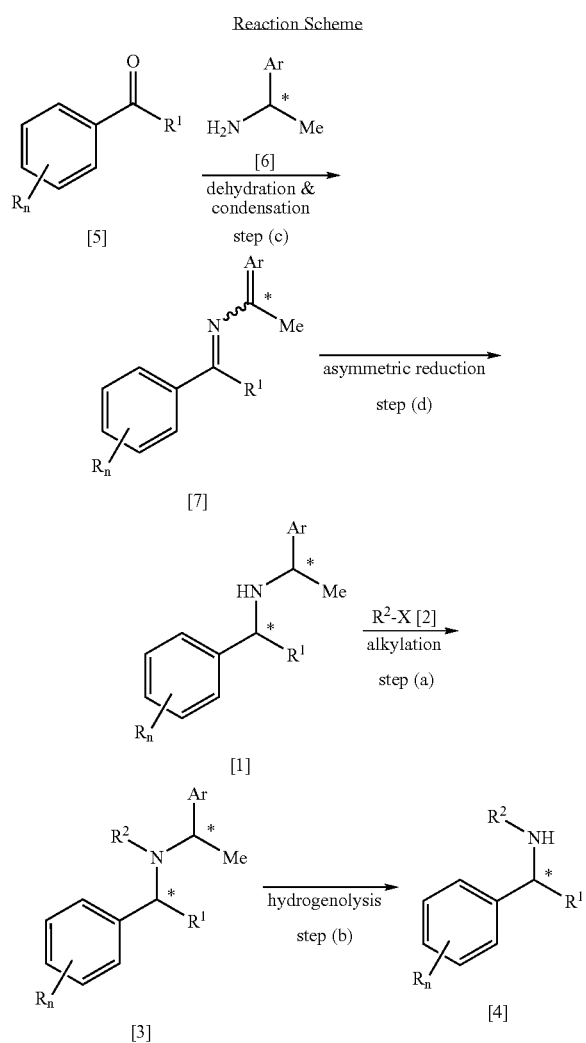

According to the present invention, it is possible to produce the target compound of the formula 4 with high optical purity by conducting the above process comprising the sequential steps of (c), (d), (a) and (b), using an optically active primary amine of the formula 6, which is relatively low in price, as an asymmetry source.

The dehydration and condensation of the step (c) are described in detail in the following. It is possible to conduct the step (c) by reacting a fluoro-, trifluoromethyl- or trifluoromethoxy-substituted phenyl alkyl ketone, represented by the formula 5, with an optically active primary amine represented by the formula 6 in the presence of an acid catalyst, thereby producing an optically active imine represented by the formula 7 (see the above reaction scheme).

As stated above, R in the formula 5 represents a fluorine atom, trifluoromethyl group or trifluoromethoxy group, and n in the formula 5 is an integer of from 1 to 5. Furthermore, each R may take any substitution position on the benzene ring of the formula 5. Examples of $(R)_n$ of the formula 5 include 2-fluoro, 3-fluoro, 4-fluoro, 2,3-difluoro, 2,4-difluoro, 2,5-difluoro, 2,6-difluoro, 3,4-difluoro, 3,5-difluoro, 2,3,4-trifluoro, 3,4,5-trifluoro, 2,4,5-trifluoro, 2,3,5-trifluoro, 2,3,6-trifluoro, 2,4,6-trifluoro, 2,3,5,6-tetrafluoro, 2,4,5,6-tetrafluoro, 3,4,5,6-tetrafluoro, 2,3,4,5,6-pentafluoro, 2-trifluoromethyl, 3-trifluoromethyl, 4-trifluoromethyl, 2,3-bis(trifluoromethyl), 2,4-bis(trifluoromethyl), 2,5-bis(trifluoromethyl), 2,6-bis(trifluoromethyl), 3,4-bis(trifluoromethyl), 3,5-bis(trifluoromethyl), 2,3,4-tris(trifluoromethyl), 3,4,5-tris(trifluoromethyl), 2,4,5-tris(trifluoromethyl), 2,3,5-tris(trifluoromethyl), 2,3,6-tris(trifluoromethyl), 2,4,6-tris(trifluoromethyl), 2,3,5,6-tetrakis(trifluoromethyl), 2,4,5,6-tetrakis(trifluoromethyl), 3,4,5,6-tetrakis(trifluoromethyl), 2,3,4,5,6-pentakis(trifluoromethyl), 2-trifluoromethoxy, 3-trifluoromethoxy, 4-trifluoromethoxy, 2,3-bis(trifluoromethoxy), 2,4-bis(trifluoromethoxy), 2,5-bis(trifluoromethoxy), 2,6-bis(trifluoromethoxy), 3,4-bis(trifluoromethoxy), 3,5-bis(trifluoromethoxy), 2,3,4-tris(trifluoromethoxy), 3,4,5-tris(trifluoromethoxy), 2,4,5-tris(trifluoromethoxy), 2,3,5-tris(trifluoromethoxy), 2,3,6-tris(trifluoromethoxy), 2,4,6-tris(trifluoromethoxy), 2,3,5,6-tetrakis(trifluoromethoxy), 2,4,5,6-tetrakis(trifluoromethoxy), 3,4,5,6-tetrakis(trifluoromethoxy), and 2,3,4,5,6-pentakis(trifluoromethoxy).

As stated above, $R^1$ in the formula 5 represents an alkyl group having a carbon atom number of from 1 to 6. Examples of $R^1$ include methyl, ethyl, 1-propyl, 2-propyl, cyclopropyl, 1-butyl, 2-butyl, 2-methyl-1-propyl, t-butyl, cyclobutyl, 1-pentyl, 2-pentyl, 3-pentyl, neopentyl, t-amyl, cyclopentyl, 1-hexyl, 2-hexyl, 3-hexyl, and cyclohexyl.

Although some of the phenyl alkyl ketones represented by the formula 5 are novel compounds depending on the types of $(R)_n$ and $R^1$, they can be produced, based on the disclosure of Tetrahedron Letters No. 53, pp. 4647-4650, 1970.

As stated above, Ar in the formula 6 represents a phenyl, 1-naphthyl or 2-naphthyl. Of these, phenyl and 2-naphthyl are preferable, and phenyl is more particularly preferable.

The optically active primary amine of the formula 6 may be in R configuration or S configuration in terms of stereochemistry. Either R configuration or S configuration may be used as the raw material of the step (c) depending on the absolute configuration of the target product.

In the step (c), the primary amine of the formula 6 may have an optical purity of not lower than 98% ee (% ee represents enantiomeric excess).

In the step (c), the amount of the primary amine of the formula 6 may be at least one equivalent, preferably 1-10 equivalents, more preferably 1-5 equivalents, per equivalent of the phenyl alkyl ketone of the formula 5.

It is possible to use an acid catalyst in the step (c) to make an acidic condition. The acid catalyst may be selected from organic acids (e.g., benzenesulfonic acid, p-toluenesulfonic acid, and 10-camphorsulfonic acid) and inorganic acids (e.g., hydrochloric acid, sulfuric acid, phosphoric acid, zinc chloride, and titanium tetrachloride). Of these, p-toluenesulfonic acid, sulfuric acid, and zinc chloride are preferable. In particular, p-toluenesulfonic acid and zinc chloride are more preferable.

The acid catalyst of the step (c) may be in a catalytic amount, preferably 0.001-0.9 equivalents, more preferably 0.005-0.5 equivalents, per equivalent of the phenyl alkyl ketone of the formula 5.

The step (c) is dehydration and condensation of a phenyl alkyl ketone represented by the formula 5 and an optically active primary amine represented by the formula 6. Therefore, the reaction can be conducted in the presence of an acid catalyst, while water as a by-product is removed. It is preferable to conduct the reaction under reflux using a solvent that is immiscible with water, that has a specific gravity lower than that of water, and that forms an azeotropic mixture with water, while water as a by-product is removed by a Dean-Stark trap.

The reaction solvent of the step (c) is preferably an aromatic hydrocarbon such as benzene, toluene, ethylbenzene, xylene, and mesitylene, particularly preferably toluene. These solvents can be used alone or in combination.

In the step (c), the reaction solvent is used in an amount such that the amount of water theoretically produced in the reaction can be separated from the reaction liquid as an azeotropic mixture of water and the reaction solvent. It is, however, possible to extremely lower the amount of the reaction solvent by using a Dean-Stark trap.

The reaction of the step (c) can be conducted at a temperature from the azeotrope temperature, at which an azeotropic mixture of water and the reaction solvent is boiled, to the boiling point of the reaction solvent. It is preferably in the vicinity of the boiling point of the reaction solvent.

Although the reaction of the step (c) may terminate within 120 hr, the reaction time may vary depending on the types of the substrates used and the reaction conditions. Therefore, it is preferable to terminate the reaction after confirming that the raw material was almost completely consumed, by checking the progress of the reaction by a suitable analytical technique (e.g., gas chromatography, thin layer chromatography, HPLC and NMR).

It is possible to obtain a crude product of the step (c) by conducting an ordinary post-treatment after the reaction. In case that the primary amine has been used in an excessive amount, it is possible to selectively remove the unreacted primary amine by washing an organic layer containing an optically active imine of the formula 7 (i.e., the product of the step (c)), with an ammonium chloride aqueous solution. According to need, the crude product can be subjected to a purification such as the use of activated carbon, distillation, recrystallization, or column chromatography, thereby obtaining an optically active imine of the formula 7 with high chemical purity.

In terms of the double bond geometry, the optically active imine of the formula 7 may be in the form of E geometry or Z geometry. The relative amounts of these geometries in the resulting imine may change depending on the reaction substrates used and the reaction conditions.

The step (d) is described in detail in the following. As stated above, the step (d) is conducted by reacting the imine of the formula 7 with a hydride reducing agent.

Since the product of the step (d), an optically active secondary amine of the formula 1, has two stereocenters (chiral carbons), there are four possible stereoisomers, R—R configuration, S—R configuration, R—S configuration and S—S configuration, where the letter before the hyphen represents the absolute configuration of the 1-(fluoro, trifluoromethyl or trifluoromethoxy-substituted phenyl)alkyl group side, and where the letter after the hyphen represents the absolute configuration of the α-arylethyl group (chiral auxiliary agent) side. The four stereoisomers may be suitably selected depending on the absolute configuration of the target product.

A hydride reducing agent to be used in the step (d) can be selected from (1) aluminium hydrides such as $(i-Bu)_2AlH$, $(i-Bu)_3Al$, $[2,6-(t-Bu)_2-4-Me-Ph]Al(i-Bu)_2$, $LiAlH_4$, $LiAlH(OMe)_3$, $LiAlH(O-t-Bu)_3$, and $NaAlH_2(OCH_2CH_2OCH_3)_2$; (2) boron hydrides such as diborane, $BH_3.THF$, $BH_3.SMe_2$, $BH_3.NMe_3$, 9-BBN, $NaBH_4$, $NaBH_4$—$CeCl_3$, $LiBH_4$, $Zn(BH_4)_2$, $Ca(BH_4)_2$, $Lin-BuBH_3$, $NaBH(OMe)_3$, $NaBH(OAc)_3$, $NaBH_3CN$, $Et_4NBH_4$, $Me_4NBH(OAc)_3$, $(n-Bu)_4NBH_3CN$, $(n-Bu)_4NBH(OAc)_3$, $Li(s-Bu)_3BH$, $K(s-Bu)_3BH$, $LiSia_3BH$, $KSia_3BH$, $LiEt_3BH$, $KPh_3BH$, $(Ph_3P)_2CuBH_4$, $ThxBH_2$, $Sia_2BH$, catecholborane, $IpcBH_2$, and $Ipc_2BH$; and (3) silicon hydrides such as $Et_3SiH$, $PhMe_2SiH$, $Ph_2SiH_2$, and $PhSiH_3$—$Mo(CO)_6$, where Bu represents a butyl group, Ph represents a phenyl group, Me represents a methyl group, THF represents tetrahydrofuran, 9-BBN represents 9-borabicyclo[3.3.1]nonane, Ac represents an acetyl group, Sia represents a thiamyl group, Et represents an ethyl group, Thx represents a thexyl group, and Ipc represents an isopinocampheyl group. Of these, preferable examples are $LiAlH_4$, diborane, $NaBH_4$, and $LiBH_4$. In particular, $NaBH_4$ is more preferable. It is possible to use a combination of at least one of these hydrides and at least one of various inorganic salts.

In the step (d), the hydride reducing agent may be in an amount of 0.25 equivalents or greater, preferably 0.25-10 equivalents, more preferably 0.25-7 equivalents, per equivalent of the imine of the formula 7.

A reaction solvent usable in the step (d) is not particularly limited. Its examples are (1) aliphatic hydrocarbons such as n-pentane, n-hexane, cyclohexane, and n-heptane; (2) aromatic hydrocarbons such as benzene, toluene, ethylbenzene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and 1,4-dioxane; (5) esters such as ethyl acetate and n-butyl acetate; (6) nitriles such as acetonitrile and propionitrile; (7) alcohols such as methanol, ethanol, n-propanol, and i-propanol; and (8) carboxylic acids such as acetic acid, propionic acid, and butyric acid. Of these, preferable examples are diethyl ether, tetrahydrofuran, t-butyl methyl ether, methanol, ethanol, and i-propanol. In particular, tetrahydrofuran, methanol, ethanol, and i-propanol are more preferable. It is possible to use a single solvent or a mixture of at least two of these.

The amount of the reaction solvent usable in the step (d) is not particularly limited. It may be at least one part by volume, preferably 1-50 parts by volume, more preferably 1-20 parts by volume, per one part by volume of the imine of the formula 7.

The reaction of the step (d) may be conducted at a temperature of from $-100°$ C. to $+100°$ C., preferably from $-80°$ C. to $+80°$ C., more preferably from $-60°$ C. to $+60°$ C.

Although the reaction of the step (d) may terminate within 72 hr, the reaction time may vary depending on the types of the substrates used and the reaction conditions. Therefore, it is preferable to terminate the reaction after confirming that the raw material was almost completely consumed, by checking the progress of the reaction by a suitable analytical technique (e.g., gas chromatography, thin layer chromatography, HPLC and NMR).

It is possible to obtain a crude product of the step (d) by conducting an ordinary post-treatment after the reaction. According to need, the crude product can be subjected to a purification such as the use of activated carbon, distillation, recrystallization, or column chromatography, thereby obtaining an optically active secondary amine of the formula 1 with high chemical purity.

After the step (d), it is possible to improve the secondary amine in diastereomeric excess by a process comprising the steps of:

(e) converting the secondary amine into a salt of an inorganic acid or organic acid; and (f) subjecting the salt to a recrystallization.

The inorganic acid of the step (e) may be selected from carbonic acid, hydrochloric acid, sulfuric acid, nitric acid, hydrobromic acid, hydroiodic acid, phosphoric acid, boric acid, perchloric acid, and the like.

The organic acid of the step (e) may be selected from (1) aliphatic carboxylic acids such as acetic acid, propionic acid, butyric acid, isobutyric acid, valeric acid, isovaleric acid, hexanoic acid, heptanoic acid, cyclohexanecarboxylic acid, octanoic acid, phenylacetic acid and 3-phenylpropionic acid; (2) haloalkylcarboxylic acids such as chloroacetic acid, dichloroacetic acid, trichloroacetic acid, fluoroacetic acid, difluoroacetic acid, trifluoroacetic acid, bromoacetic acid, iodoacetic acid, 2-chloropropionic acid and 3-chloropropionic acid; (3) unsaturated carboxylic acids such as acrylic acid, crotonic acid, citraconic acid, maleic acid, fumaric acid and cis- or trans-cinnamic acid; (4) aromatic carboxylic acids such as benzoic acid, o-, m- or p-toluic acid, o-, m- or p-fluorobenzoic acid, o-, m- or p-chlorobenzoic acid, o-, m- or p-bromobenzoic acid, o-, m- or p-iodobenzoic acid, o, m- or p-hydroxybenzoic acid, o-, m- or p-anisic acid, o-, m- or p-aminobenzoic acid, o-, m- or p-nitrobenzoic acid, o-, m- or p-cyanobenzoic acid, m- or p-benzenedicarboxylic acid (phthalic acid, isophthalic acid or terephthalic acid), α-, β- or γ-picolinic acid, 2,6-pyridinedicarboxylic acid and 1- or 2-naphthoic acid; (5) sulfonic acids such as methanesulfonic acid, chloromethanesulfonic acid, trifluoromethanesulfonic acid, benzenesulfonic acid, p-toluenesulfonic acid and p-phenolsulfonic acid; (6) optically active carboxylic acids such as lactic acid, malic acid, tartaric acid, dibenzoyltartaric acid, 2-phenylpropionic acid, mandelic acid, camphoric acid and cis-2-benzamidocyclohexanecarboxylic acid; (7) optically active sulfonic acids such as phenylethanesulfonic acid and 10-camphorsulfonic acid; (8) optically active phosphoric acids such as 2,2'-(1,1'-binaphthyl)phosphoric acid; (9) optically active amino acids such as 4-aminobutyric acid, phenylglycine and aspartic acid; (10) optically active N-acylamino acids such as pyroglutamic acid, N-acetyl-3,5-dibromo-tyrosine, N-acyl-phenylalanine, N-acyl-aspartic acid, N-acylglutamic acid and N-acylproline (wherein, N-acyl group represents acetyl group, benzyloxycarbonyl group, benzoyl group, benzenesulfonyl group, p-toluenesulfonyl group and the like), and (11) other organic acids such as formic acid, oxalic acid, malonic acid, succinic acid, adipic acid, pimelic acid, cyanoacetic acid, citric acid, glycolic acid, glyoxylic acid, pyruvic acid, levulinic acid, oxaloacetic acid, mercaptoacetic acid, phenoxyacetic acid and picric acid. Although the optically active carboxylic acids, the optically active sulfonic acids, the optically active phosphoric acids, the optically active amino acids or the optically active N-acylamino acids exist in R configuration or in S configuration, their enantiomers may be suitably selected for use. Among these, fumaric acid, phthalic acid and p-toluenesulfonic acid are more preferable.

In the step (e), the inorganic or organic acid may be in an amount of 0.3 equivalents or greater, preferably 0.3-5 equivalents, more preferably 0.3-3 equivalents, per equivalent of the secondary amine of the formula 1.

The actual operation of the steps (e) and (f) can suitably be selected in view of the combination of the inorganic or organic acid and the optically active secondary amine. For example, it is possible to conduct the steps (e) and (f) by directly adding the optically active secondary amine and an inorganic or organic acid into a recrystallization solvent, followed by mixing. Alternatively, it is possible to mix a solution of the optically active secondary amine with a solution of the inorganic or organic acid to conduct the steps (e) and (f).

The recrystallization solvent of the steps (e) and (f) is not particularly limited as long as it does not react with the optically active secondary amine, the inorganic or organic acid, and the salt obtained by the step (e). The recrystallization solvent can suitably be selected in view of, for example, (a) the diastereomeric excess prior to purification of the salt using the recrystallization solvent, (b) the diastereomeric excess prior after that, and (c) recovery.

The recrystallization solvent of the steps (e) and (f) may be selected from (1) aliphatic hydrocarbons such as n-pentane, n-hexane, c-hexane, and n-heptane; (2) aromatic hydrocarbons such as benzene, toluene, ethylbenzene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and 1,4-dioxane; (5) ketones such as acetone, methyl ethyl ketone, and methyl isobutyl ketone; (6) esters such as ethyl acetate and n-butyl acetate; (7) nitriles such as acetonitrile and propionitrile; (8) alcohols such as methanol, ethanol, n-propanol, i-propanol, and n-butanol; and (9) water. Of these, preferable examples are n-hexane, n-heptane, toluene, methylene chloride, t-butyl methyl ether, acetone, ethyl acetate, acetonitrile, methanol, ethanol, n-propanol, and i-propanol. It is possible to use a single solvent or a mixture of at least two of these.

The amount of the recrystallization solvent of the steps (e) and (f) is not particularly limited, as long as the product (salt) of the steps (e) and (f) is completely or partially dissolved therein under heating. It can suitably be selected in view of, for example, (a) the diastereomeric excess prior to purification of the salt using the recrystallization solvent, (b) the diastereomeric excess after that, and (c) recovery. For example, the recrystallization solvent may be in an amount of at least 1 part by volume, preferably 1-100 parts by volume, more preferably 1-50 parts by volume, relative to the salt of the secondary amine of the formula 1.

Although the secondary amine prior to the steps (e) and (f) is not particularly limited in diastereomeric excess, it is preferably 10% de (% de represents diastereomeric excess) or greater.

The recrystallization proceeds smoothly and efficiently by adding seed crystals. The seed crystals are in an amount of preferably from 1/10,000 to 1/10 parts by weight, more preferably from 1/5,000 to 1/20 parts by weight, relative to one part by weight of the salt (product) of the step (e) prior to purification.

The temperature for conducting the recrystallization may suitably be selected in view of boiling point and freezing point of the recrystallization solvent. For example, the recrystallization may be conducted by dissolving the salt prior to purification in a recrystallization solvent at a temperature of from room temperature (e.g., 25° C.) to a temperature close to boiling point of the recrystallization solvent and then by precipitating crystals at a temperature of −40 to +80° C.

The precipitated crystals can be recovered by filtration or the like to increase the diastereomeric excess of the crystals.

With this, it is possible to make the salt (product) of the steps (e) and (f) have high purity. Its purity can be improved further by repeating the recrystallization operation. The salt itself obtained by the steps (e) and (f) can be used in the alkylation of the step (a). In this case, it suffices to conduct the alkylation by using a base in an amount sufficient for neutralizing the salt into a free base in the reaction system. Alternatively, the salt may be neutralized into a free base to be used in the step (a). In this case, the salt can be neutralized by an inorganic base aqueous solution, followed by extraction with an organic solvent. With this, it is possible to efficiently collect the free base.

By conducting the purification of the steps (e) and (f), it is possible to precipitate crystals of a major isomer contained in the reaction mixture, thereby improving the optical purity. After the recrystallization, the resulting mother liquor may be subjected to procedures similar to the above recrystallization. With this, a minor isomer may predominantly be crystallized.

The alkylation of the step (a) is described in detail in the following. As stated above, the step (a) is conducted by reacting an optically active secondary amine of the formula 1 with an alkylation agent of the formula 2 in the presence of a base, thereby producing an optically active tertiary amine of the formula 3.

The absolute configurations about the two chiral carbons of the secondary amine do not change by the alkylation. In other words, the tertiary amine will be in the same stereoisomer (e.g., R—R configuration) as that of the secondary amine.

As stated above, $R^2$ in the formula 2 represents an alkyl group having a carbon atom number of from 1 to 6. It may be selected from methyl, ethyl, 1-propyl, 2-propyl, cyclopropyl, 1-butyl, 2-butyl, 2-methyl-1-propyl, t-butyl, cyclobutyl, 1-pentyl, 2-pentyl, 3-pentyl, neopentyl, t-amyl, cyclopentyl, 1-hexyl, 2-hexyl, 3-hexyl, cyclohexyl and the like.

The leaving group (represented by X) of the alkylation agent may be selected from chlorine, bromine, iodine, mesylate group ($MeSO_2O$), monochloromesylate group ($CH_2ClSO_2O$), tosylate group (p-$MeC_6H_4SO_2O$), triflate group ($CF_3SO_2O$) and the like. Of these, bromine, iodine, mesylate group, tosylate group, and triflate group are preferable, and bromine, iodine and mesylate group are more preferable.

The amount of the alkylation agent may be at least one equivalent, preferably 1-50 equivalents, 1-30 equivalents, per equivalent of the secondary amine.

The base used in the step (a) may be selected from (1) organic bases such as trimethylamine, triethylamine, diisopropylethylamine, tri-n-butylamine, dimethyllaurylamine, dimethylaminopyridine, N,N-dimethylaniline, dimethylbenzylamine, 1,8-diazabicyclo[5.4.0]undec-7-ene, 1,4-diazabicyclo[2.2.2]octane, pyridine, 2,4-lutidine, 2,5-lutidine, 2,6-lutidine, 3,4-lutidine, 3,5-lutidine, 2,4,6-trimethylpyridine, pyrimidine, and pyridazine; and (2) inorganic bases such as lithium hydride, sodium hydride, potassium hydride, calcium hydride, lithium carbonate, sodium carbonate, potassium carbonate, cesium carbonate, sodium hydrogencarbonate, potassium hydrogencarbonate, lithium hydroxide, sodium hydroxide, and potassium hydroxide. Of these, triethylamine, dimethylaminopyridine, 1,8-diazabicyclo[5.4.0]undec-7-ene, 2,6-lutidine, sodium hydride, sodium carbonate, potassium carbonate, sodium hydrogencarbonate, and potassium hydrogencarbonate are preferable. In particular, triethylamine, 1,8-diazabicyclo[5.4.0]undec-7-ene, 2,6-lutidine, sodium hydride, sodium carbonate, and potassium carbonate are more preferable. These bases can be used alone or in combination.

The amount of the base may be at least one equivalent, preferably 1-50 equivalents, more preferably 1-30 equivalents, per equivalent of the secondary amine.

A reaction solvent usable in the step (a) is not particularly limited. Its examples are (1) aliphatic hydrocarbons such as n-pentane, n-hexane, cyclohexane, and n-heptane; (2) aromatic hydrocarbons such as benzene, toluene, ethylbenzene, xylene, and mesitylene; (3) halogenated hydrocarbons such as methylene chloride, chloroform, and 1,2-dichloroethane; (4) ethers such as diethyl ether, tetrahydrofuran, t-butyl methyl ether, and 1,4-dioxane; (5) esters such as ethyl acetate and n-butyl acetate; (6) amides such as hexamethylphosphoric triamide, N,N-dimethylformamide, N,N-dimethylacetamide, and N-methylpyrolidone. (7) nitriles such as acetonitrile and propionitrile; (8) alcohols such as methanol, ethanol, n-propanol, and i-propanol; and (9) dimethylsulfoxide. Of these, preferable examples are toluene, 1,2-dichloroethane, tetrahydrofuran, ethyl acetate, N,N-dimethylformamide, N,N-dimethylacetamide, acetonitrile, and dimethylsulfoxide are preferable. In particular, tetrahydrofuran, N,N-dimethylformamide, N,N-dimethylacetamide, acetonitrile, and dimethylsulfoxide are more preferable. It is possible to use a single solvent or a mixture of at least two of these.

The amount of the reaction solvent usable in the step (a) is not particularly limited. It may be at least one part by volume, preferably 1-50 parts by volume, more preferably 1-20 parts by volume, per one part by volume of the secondary amine.

The reaction of the step (a) may be conducted at a temperature of from −10° C. to +200° C., preferably from 0° C. to +175° C., more preferably from +10° C. to +150° C.

Although the reaction of the step (a) may terminate within 72 hr, the reaction time may vary depending on the types of the substrates used and the reaction conditions. Therefore, it is preferable to terminate the reaction after confirming that the raw material was almost completely consumed, by checking the progress of the reaction by a suitable analytical technique (e.g., gas chromatography, thin layer chromatography, HPLC and NMR).

It is possible to obtain a crude product of the step (a) by conducting an ordinary post-treatment after the reaction. According to need, the crude product can be subjected to a purification such as the use of activated carbon, distillation, recrystallization, or column chromatography, thereby obtaining an optically active tertiary amine of the formula 3 with high chemical purity.

The hydrogenolysis of the step (b) is described in detail in the following. The hydrogenolysis is achieved by reacting the tertiary amine with hydrogen, thereby producing the target product of the present invention, the N-monoalkyl derivative of the formula 4.

In case that the tertiary amine is in the R—R configuration or R—S configuration, R configuration becomes excessive in the product of the step (b). In case that the tertiary amine is in the S—S configuration or S—R configuration, S configuration becomes excessive in the product of the step (b).

The hydrogenolysis can proceed well by a catalytic reduction using a transition metal complex as a catalyst. This transition metal complex can be selected from (1) platinum catalysts such as platinum oxide, platinum/active carbon and platinum black; (2) nickel catalysts such as reduced nickel, Raney nickel and platinum-Raney nickel; (3) cobalt catalysts such as Raney cobalt; (4) ruthenium catalysts such as ruthenium oxide and ruthenium/active carbon; (5) rhodium catalysts such as rhodium/active carbon, rhodium/alumina and rhodium-platinum oxide; (6) iridium catalysts such as iridium black; and (7) palladium catalysts such as palladium/active carbon, palladium hydroxide, palladium black, palladium/barium sulfate, palladium/strontium carbonate, palladium/calcium carbonate, palladium/calcium carbonate-lead diacetate, palladium/barium sulfate-quinoline, palladium/alumina, palladium sponge, palladium chloride, palladium acetate, palladium acetylacetonate, bis(dibenzylideneacetone)palladium, tetrakis(triphenylphosphine)palladium, dichloro[bis(triphenylphosphine)]palladium, dichloro[bis(diphenylphosphino)methane]palladium, dichloro[bis(diphenylphosphino)ethane]palladium, dichloro[1,3-bis(diphenylphosphino)propane]palladium, dichloro[1,4-bis(diphenylphosphino)butane]palladium, dichloro(1,5-cyclooctadiene)palladium, dichloro[bis(benzonitrile)]palladium, dichloro[bis(acetonitrile)]palladium, and [bis(triphenylphosphine)]palladium acetate. Among these, platinum catalysts, rhodium catalysts and palladium catalysts are preferable, and platinum/active carbon, rhodium/active carbon and palladium/active carbon are particularly more preferable. These catalysts can be used alone or in combination. In the case of using a catalyst in which a metal is loaded onto a support, the loaded amount is 0.1-50 wt %, preferably 0.5-30 wt %, and particularly more preferably 1-20 wt %. In addition, in order to enhance safety during handling or to prevent oxidation of the metal surface, it is possible to use a transition metal complex stored in water or mineral oil.

The transition metal complex (in terms of metal contained in the complex) may be in an amount of 0.5 wt % or less, preferably 0.001-0.4 wt %, more preferably 0.005-0.3 wt %, based on the total weight (100 wt %) of the tertiary amine.

The hydrogenolysis of the step (b) may be conducted by using hydrogen in an amount of at least one equivalent, per equivalent of the tertiary amine. It is, however, usual to use hydrogen excessively due to the hydrogenolysis under a hydrogen atmosphere. The hydrogen pressure may be 2 MPa or less, preferably 0.01-1.5 MPa, more preferably 0.05-1.0 MPa.

The hydrogenolysis can proceed smoothly by adding an organic or inorganic acid as an additive. Its examples include organic acids such as acetic acid, propionic acid, butyric acid, p-toluenesulfonic acid, and 10-camphorsulfonic acid; and inorganic acids such as hydrochloric acid, sulfuric acid, nitric acid, hydrobromic acid, and hydroiodic acid. Of these, acetic acid, propionic acid, hydrochloric acid, sulfuric acid, and hydrobromic acid are preferable, and acetic acid, hydrochloric acid and sulfuric acid are more preferable.

The additive of the hydrogenolysis may be in an amount of 0.1 equivalents or more, preferably 0.1-100 equivalents, more preferably 0.1-50 equivalents, per equivalent of the tertiary amine.

The reaction solvent usable in the step (b) may be selected from (1) aliphatic hydrocarbons such as n-pentane, n-hexane, c-hexane, and n-heptane; (2) aromatic hydrocarbons such as benzene, toluene, ethylbenzene, xylene, and mesitylene; (3) ethers such as diethyl ether, tetrahydrofuran, t-butyl methyl ether, and 1,4-dioxane; (4) esters such as ethyl acetate and n-butyl acetate; (5) alcohols such as methanol, ethanol, n-propanol, and i-propanol; (6) carboxylic acids such as acetic acid, propionic acid, and butyric acid; (7) acidic aqueous solutions such as hydrochloric acid, sulfuric acid, hydrobromic acid, p-toluenesulfonic acid and 10-camphorsulfonic acid; and (8) water. Among these, toluene, ethyl acetate, methanol, ethanol, i-propanol, acetic acid and hydrochloric acid aqueous solution are preferable, while methanol, ethanol, i-propanol, acetic acid and hydrochloric acid aqueous solution are particularly more preferable. These reaction solvents can be used alone or in combination.

The amount of the reaction solvent usable in the hydrogenolysis is not particularly limited. It may be at least one part by volume, preferably 1-100 parts by volume, more preferably 1-50 parts by volume, per one volume of the tertiary amine.

The hydrogenolysis may be conducted at a temperature of +40° C. or higher, preferably +40° C. to +200° C., more preferably +40° C. to +150° C.

Although the reaction of the step (b) may terminate within 72 hr, the reaction time may vary depending on the types of the substrates used and the reaction conditions. Therefore, it is preferable to terminate the reaction after confirming that the raw material was almost completely consumed, by checking the progress of the reaction by a suitable analytical technique (e.g., gas chromatography, thin layer chromatography, HPLC and NMR).

It is possible to obtain a crude product of the step (b) by conducting an ordinary post-treatment after the reaction. In case that an organic or inorganic acid has been added as the additive in the step (b), it is possible to efficiently collect the target free base by neutralizing the reaction mixture with an inorganic base aqueous solution, followed by extraction with an organic solvent. According to need, the crude product can be subjected to a purification such as the use of activated carbon, distillation, recrystallization, or column chromatography, thereby obtaining an optically active 1-(fluoro-, trifluoromethyl- or trifluoromethoxy-substituted phenyl)alkylamine N-monoalkyl derivative of the formula 4 with high optical purity and high chemical purity.

Nonlimitative examples of the target product represented by the formula 4, which can be produced by the present invention, include
(R)-1-(2-fluorophenyl)ethylamine N-monomethyl,
(S)-1-(2-fluorophenyl)ethylamine N-monomethyl,
(R)-1-(3-fluorophenyl)ethylamine N-monomethyl,
(S)-1-(3-fluorophenyl)ethylamine N-monomethyl,
(R)-1-(4-fluorophenyl)ethylamine N-monomethyl,
(S)-1-(4-fluorophenyl)ethylamine N-monomethyl,
(R)-1-(3,5-difluorophenyl)ethylamine N-monomethyl,
(S)-1-(3,5-difluorophenyl)ethylamine N-monomethyl,
(R)-1-(2-fluorophenyl)propylamine N-monomethyl,
(S)-1-(2-fluorophenyl)propylamine N-monomethyl,
(R)-1-(3-fluorophenyl)propylamine N-monomethyl,
(S)-1-(3-fluorophenyl)propylamine N-monomethyl,
(R)-1-(4-fluorophenyl)propylamine N-monomethyl,
(S)-1-(4-fluorophenyl)propylamine N-monomethyl,
(R) 1-(3,5-difluorophenyl)propylamine N-monomethyl,
(S)-1-(3,5-difluorophenyl)propylamine N-monomethyl,
(R)-1-(2-fluorophenyl)pentylamine N-monomethyl,
(S)-1-(2-fluorophenyl)pentylamine N-monomethyl,
(R)-1-(3-fluorophenyl)pentylamine N-monomethyl,
(S)-1-(3-fluorophenyl)pentylamine N-monomethyl,
(R)-1-(4-fluorophenyl)pentylamine N-monomethyl,
(S)-1-(4-fluorophenyl)pentylamine N-monomethyl,
(R)-1-(3,5-difluorophenyl)pentylamine N-monomethyl,
(S)-1-(3,5-difluorophenyl)pentylamine N-monomethyl,
(R)-1-(2-fluorophenyl)ethylamine N-monoethyl,
(S)-1-(2-fluorophenyl)ethylamine N-monoethyl,
(R)-1-(3-fluorophenyl)ethylamine N-monoethyl,
(S)-1-(3-fluorophenyl)ethylamine N-monoethyl,
(R)-1-(4-fluorophenyl)ethylamine N-monoethyl,
(S)-1-(4-fluorophenyl)ethylamine N-monoethyl, (R)-1-(3,5-difluorophenyl)ethylamine N-monoethyl,
(S)-1-(3,5-difluorophenyl)ethylamine N-monoethyl,
(R)-1-(2-fluorophenyl)propylamine N-monoethyl,
(S)-1-(2-fluorophenyl)propylamine N-monoethyl,
(R)-1-(3-fluorophenyl)propylamine N-monoethyl,
(S)-1-(3-fluorophenyl)propylamine N-monoethyl,
(R)-1-(4-fluorophenyl)propylamine N-monoethyl,
(S)-1-(4-fluorophenyl)propylamine N-monoethyl,
(R)-1-(3,5-difluorophenyl)propylamine N-monoethyl,
(S)-1-(3,5-difluorophenyl)propylamine N-monoethyl,
(R)-1-(2-fluorophenyl)pentylamine N-monoethyl,
(S)-1-(2-fluorophenyl)pentylamine N-monoethyl,
(R)-1-(3-fluorophenyl)pentylamine N-monoethyl,
(S)-1-(3-fluorophenyl)pentylamine N-monoethyl,
(R)-1-(4-fluorophenyl)pentylamine N-monoethyl,
(S)-1-(4-fluorophenyl)pentylamine N-monoethyl,
(R) 1-(3,5-difluorophenyl)pentylamine N-monoethyl,
(S)-1-(3,5-difluorophenyl)pentylamine N-monoethyl,
(R)-1-(2-trifluoromethylphenyl)ethylamine N-monomethyl,
(S)-1-(2-trifluoromethylphenyl)ethylamine N-monomethyl,
(R)-1-(3-trifluoromethylphenyl)ethylamine N-monomethyl,
(S)-1-(3-trifluoromethylphenyl)ethylamine N-monomethyl,
(R)-1-(4-trifluoromethylphenyl)ethylamine N-monomethyl,
(S)-1-(4-trifluoromethylphenyl)ethylamine N-monomethyl,
(R)-1-(3,5-bis(trifluoromethyl)phenyl)ethylamine N-monomethyl,
(S)-1-(3,5-bis(trifluoromethyl)phenyl)ethylamine N-monomethyl,
(R)-1-(2-trifluoromethylphenyl)propylamine N-monomethyl,
(S)-1-(2-trifluoromethylphenyl)propylamine N-monomethyl,
(R)-1-(3-trifluoromethylphenyl)propylamine N-monomethyl,
(S)-1-(3-trifluoromethylphenyl)propylamine N-monomethyl,
(R)-1-(4-trifluoromethylphenyl)propylamine N-monomethyl,
(S)-1-(4-trifluoromethylphenyl)propylamine N-monomethyl,
(R)-1-(3,5-bis(trifluoromethyl)phenyl)propylamine N-monomethyl,
(S)-1-(3,5-bis(trifluoromethyl)phenyl)propylamine N-monomethyl,
(R)-1-(2-trifluoromethylphenyl)pentylamine N-monomethyl,
(S)-1-(2-trifluoromethylphenyl)pentylamine N-monomethyl,
(R)-1-(3-trifluoromethylphenyl)pentylamine N-monomethyl,
(S)-1-(3-trifluoromethylplienyl)pentylamine N-monomethyl,
(R)-1-(4-trifluoromethylphenyl)pentylamine N-monomethyl,
(S)-1-(4-trifluoromethylphenyl)pentylamine N-monomethyl,
(R)-1-(3,5-bis(trifluoromethyl)phenyl)pentylamine N-monomethyl,
(S)-1-(3,5-bis(trifluoromethyl)phenyl)pentylamine N-monomethyl,
(R)-1-(2-trifluoromethylphenyl)ethylamine N-monoethyl,
(S)-1-(2-trifluoromethylphenyl)ethylamine N-monoethyl,
(R)-1-(3-trifluoromethylphenyl)ethylamine N-monoethyl,
(S)-1-(3-trifluoromethylphenyl)ethylamine N-monoethyl,
(R)-1-(4-trifluoromethylphenyl)ethylamine N-monoethyl,
(S)-1-(4-trifluoromethylphenyl)ethylamine N-monoethyl,
(R)-1-(3,5-bis(trifluoromethyl)phenyl)ethylamine N-monoethyl,
(S)-1-(3,5-bis(trifluoromethyl)phenyl)ethylamine N-monoethyl,
(R)-1-(2-trifluoromethylphenyl)propylamine N-monoethyl,
(S)-1-(2-trifluoromethylphenyl)propylamine N-monoethyl,
(R)-1-(3-trifluoromethylphenyl)propylamine N-monoethyl,
(S)-1-(3-trifluoromethylphenyl)propylamine N-monoethyl,
(R)-1-(4-trifluoromethylphenyl)propylamine N-monoethyl,
(S)-1-(4-trifluoromethylphenyl)propylamine N-monoethyl,
(R)-1-(3,5-bis(trifluoromethyl)phenyl)propylamine N-monoethyl,
(S)-1-(3,5-bis(trifluoromethyl)phenyl)propylamine N-monoethyl,
(R)-1-(2-trifluoromethylphenyl)pentylamine N-monoethyl,
(S)-1-(2-trifluoromethylphenyl)pentylamine N-monoethyl,
(R)-1-(3-trifluoromethylphenyl)pentylamine N-monoethyl,
(S)-1-(3-trifluoromethylphenyl)pentylamine N-monoethyl,
(R)-1-(4-trifluoromethylphenyl)pentylamine N-monoethyl,
(S)-1-(4-trifluoromethylphenyl)pentylamine N-monoethyl,
(R)-1-(3,5-bis(trifluoromethyl)phenyl)pentylamine N-monoethyl,
(S)-1-(3,5-bis(trifluoromethyl)phenyl)pentylamine N-monoethyl,
(R)-1-(2-trifluoromethoxyphenyl)ethylamine N-monomethyl,
(S)-1-(2-trifluoromethoxyphenyl)ethylamine N-monomethyl,
(R)-1-(3-trifluoromethoxyphenyl)ethylamine N-monomethyl,
(S)-1-(3-trifluoromethoxyphenyl)ethylamine N-monomethyl,
(R)-1-(4-trifluoromethoxyphenyl)ethylamine N-monomethyl,
(S)-1-(4-trifluoromethoxyphenyl)ethylamine N-monomethyl,
(R)-1-(3,5-bis(trifluoromethoxy)phenyl)ethylamine N-monomethyl,
(S)-1-(3,5-bis(trifluoromethoxy)phenyl)ethylamine N-monomethyl,
(R)-1-(2-trifluoromethoxyphenyl)propylamine N-monomethyl,
(S)-1-(2-trifluoromethoxyphenyl)propylamine N-monomethyl,
(R)-1-(3-trifluoromethoxyphenyl)propylamine N-monomethyl,
(S)-1-(3-trifluoromethoxyphenyl)propylamine N-monomethyl,
(R)-1-(4-trifluoromethoxyphenyl)propylamine N-monomethyl,
(S)-1-(4-trifluoromethoxyphenyl)propylamine N-monomethyl,
(R) 1-(3,5-bis(trifluoromethoxy)phenyl)propylamine N-monomethyl,
(S)-1-(3,5-bis(trifluoromethoxy)phenyl)propylamine N-monomethyl,
(R)-1-(2-trifluoromethoxyphenyl)pentylamine N-monomethyl,
(S)-1-(2-trifluoromethoxyphenyl)pentylamine N-monomethyl,
(R)-1-(3-trifluoromethoxyphenyl)pentylamine N-monomethyl,
(S)-1(3-trifluoromethoxyphenyl)pentylamine N-monomethyl,
(R)-1-(4-trifluoromethoxyphenyl)pentylamine N-monomethyl, (S)-1-(4-trifluoromethoxyphenyl)pentylamine N-monomethyl,
(R)-1-(3,5-bis(trifluoromethoxy)phenyl)pentylamine N-monomethyl,
(S)-1-(3,5-bis(trifluoromethoxy)phenyl)pentylamine N-monomethyl,
(R)-1-(2-trifluoromethoxyphenyl)ethylamine N-monoethyl,
(S)-1-(2-trifluoromethoxyphenyl)ethylamine N-monoethyl,
(R)-1-(3-trifluoromethoxyphenyl)ethylamine N-monoethyl,
(S)-1-(3-trifluoromethoxyphenyl)ethylamine N-monoethyl,
(R)-1-(4-trifluoromethoxyphenyl)ethylamine N-monoethyl,
(S)-1-(4-trifluoromethoxyphenyl)ethylamine N-monoethyl,
(R)-1-(3,5-bis(trifluoromethoxy)phenyl)ethylamine N-monoethyl,
(S)-1-(3,5-bis(trifluoromethoxy)phenyl)ethylamine N-monoethyl,
(R)-1-(2-trifluoromethoxyphenyl)propylamine N-monoethyl,
(S)-1-(2-trifluoromethoxyphenyl)propylamine N-monoethyl,
(R)-1-(3-trifluoromethoxyphenyl)propylamine N-monoethyl,
(S)-1-(3-trifluoromethoxyphenyl)propylamine N-monoethyl,
(R)-1-(4-trifluoromethoxyphenyl)propylamine N-monoethyl,
(S)-1-(4-trifluoromethoxyphenyl)propylamine N-monoethyl,
(R)-1-(3,5-bis(trifluoromethoxy)phenyl)propylamine N-monoethyl,
(S)-1-(3,5-bis(trifluoromethoxy)phenyl)propylamine N-monoethyl,
(R)-1-(2-trifluoromethoxyphenyl)pentylamine N-monoethyl,
(S)-1-(2-trifluoromethoxyphenyl)pentylamine N-monoethyl,
(R)-1-(3-trifluoromethoxyphenyl)pentylamine N-monoethyl,
(S)-1-(3-trifluoromethoxyphenyl)pentylamine N-monoethyl,
(R)-1-(4-trifluoromethoxyphenyl)pentylamine N-monoethyl,
(S)-1-(4-trifluoromethoxyphenyl)pentylamine N-monoethyl,
(R)-1-(3,5-bis(trifluoromethoxy)phenyl)pentylamine N-monoethyl, and
(S)-1-(3,5-bis(trifluoromethoxy)phenyl)pentylamine N-monoethyl.

The following nonlimitative examples are illustrative of the present invention.

EXAMPLE 1

SYNTHESIS OF OPTICALLY ACTIVE (S)-1-(4-FLUOROPHENYL)ETHYLAMINE N-MONOMETHYL

Step (c), Dehydration and Condensation

At first, 20.00 g (144.78 mmol, 1 eq.) of 4-fluorophenyl methyl ketone, 19.30 g (159.27 mmol, 1.10 eq.) of (S)-1-phenylethylamine, and 0.60 g (4.40 mmol, 0.03 eq.) of zinc chloride were added to 145 ml of toluene. The resulting mixture was stirred for 19 hr under a heated reflux condition, while water (by-product) was removed from a Dean-Stark trap. The resulting reaction liquid was washed with 5% sodium hydroxide aqueous solution, 1.5N ammonium chloride aqueous solution, and water. The recovered organic layer was dried with anhydrous sodium sulfate, filtrated, concentrated and vacuum-dried, thereby obtaining 35.00 g of a crude product of an optically active imine represented by the following formula.

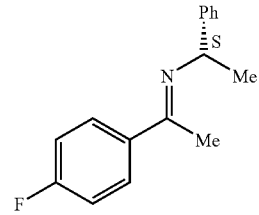

Conversion was found by gas chromatography to be 98%.
$^1$H-NMR (standard substance: TMS; solvent: CDCl$_3$), δppm: 1.53 (d, 6.6 Hz, 3H), 2.25 (s, 3H), 4.82 (q, 6.6 Hz, 1H), 7.00-7.50 (Ar—H, 7H), 7.80-7.90 (Ar—H, 2H).

Step (d), Asymmetric Reduction

At first, 35.00 g (144.78 mmol, 1 eq.) of the crude product of the optically active imine produced by the above step (c) were added to 120 ml of methanol. The resulting solution was cooled down to 0° C. Then, 5.50 g (145.39 mmol, 1.00 eq.) of sodium borohydride were added, followed by stirring for 5 hr at the same temperature. After the reaction, 1N hydrochloric acid aqueous solution was added to decompose the remaining sodium borohydride. Then, the reaction liquid was made basic by adding 1N sodium hydroxide aqueous solution, followed by extraction with toluene. The collected organic layer was washed with water, dried with anhydrous sodium sulfate, filtrated, concentrated, and vacuum-dried, thereby obtaining 35.34 g of a crude product of an optically active secondary amine represented by the following formula.

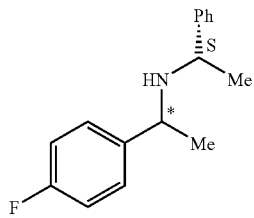

It was found by gas chromatography that conversion of the crude product was 100% and that the ratio of a diastereomer of S—S configuration to a diastereomer of R—S configuration was 93:7.

The NMR data of the crude product are as follows.
$^1$H-NMR (TMS, CDCl$_3$) of S—S configuration, δppm: 1.24 (d, 6.4 Hz, 3H), 1.27 (d, 6.4 Hz, 3H), 1.60 (br, 1H), 3.45 (q, 6.4 Hz, 1H), 3.49 (q, 6.4 Hz, 1H), 6.90-7.50 (Ar—H, 9H).

$^1$H-NMR (TMS, CDCl$_3$) of R—S configuration, δppm: 1.32 (d, 6.8 Hz, 3H), 1.35 (d, 6.8 Hz, 3H), 1.60 (br, 1H), 3.74 (q, 6.8 Hz, 2H), 6.90-7.50 (Ar—H, 9H)

Steps (e) and (f), Salt Formation and its Recrystallization 8.00 g (32.77 mmol, 1 eq.) of the crude product of the optically active secondary amine produced by the above step (d) and 5.44 g (32.75 mmol, 1.00 eq.) of phthalic acid were added to 39.5 ml of i-propanol, followed by dissolving these solutes at 50° C. The resulting solution was allowed to cool down to room temperature, followed by addition of seed crystals and then stirring for 12 hr. The precipitated crystals were filtered, washed with a small amount of n-heptane, and vacuum-dried, thereby obtaining 10.06 g of crystals of a phthalate of the optically active secondary amine, which is represented by the following formula.

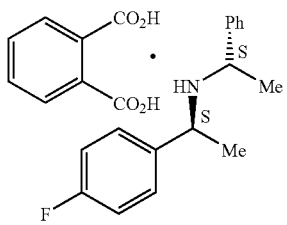

The diastereomeric excess of the crystals was determined by gas chromatography in a manner that the phthalate was turned into a free base with 1N sodium hydroxide aqueous solution. The result was 99.3% de. The total yield from the dehydration and the condensation to the salt formation and its recrystallization was 75%.

$^1$H-NMR (TMS, CDCl$_3$), δppm: 1.78 (d, 6.8 Hz, 6H), 4.03 (q, 6.8 Hz, 1H), 4.06 (q, 6.8 Hz, 1H), 7.09 (Ar—H, 2H), 7.36-7.48 (Ar—H, 7H), 7.55-7.65 (Ar—H, 2H), 8.45-8.55 (Ar—H, 2H), 10.40 (br, 3H).

Then, 1N sodium hydroxide aqueous solution was added to 6.70 g (16.36 mmol) of the crystals of the phthalate to have a basic solution, followed by extraction with toluene. The collected organic layer was washed with water and then saturated brine, dried with anhydrous sodium sulfate, filtrated, concentrated, and vacuum-dried, thereby obtaining 3.98 g of a purified product of an optically active secondary amine represented by the following formula.

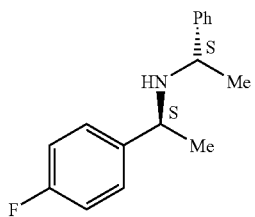

The recovery was quantitative.

$^1$H-NMR (TMS, CDCl$_3$), δppm: 1.24 (d, 6.4 Hz, 3H), 1.27 (d, 6.4 Hz, 3H), 1.60 (br, 1H), 3.45 (q, 6.4 Hz, 1H), 3.49 (q, 6.4 Hz, 1H), 6.90-7.50 (Ar—H, 9H).

Step (a), Alkylation

At first, 1.50 g (6.16 mmol, 1 eq.) of the above purified product of the optically active secondary amine, 4.38 g (30.86 mmol, 5.01 eq.) of methyl iodide, and 1.70 g (12.30 mmol, 2.00 eq.) of anhydrous potassium carbonate were added to a mixed solution of 0.6 ml of dimethylformamide and 5.6 ml of tetrahydrofuran, followed by stirring at 45-50° C. for 24 hr. After the reaction, the reaction liquid was diluted with ethyl acetate, followed by washing with saturated brine, drying with anhydrous sodium sulfate, filtration, concentration, and vacuum drying, thereby obtaining 1.99 g of a crude product of an optically active tertiary amine represented by the following formula.

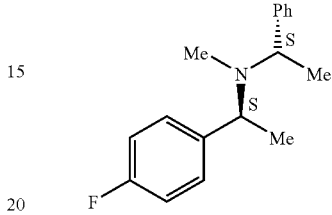

Conversion was found by gas chromatography to be 100%. Furthermore, the crude product was purified by a silica gel column chromatography (ethyl acetate:n-hexane=1:10), thereby obtaining 1.38 g of a purified product of the optically active tertiary amine. The yield was 87%.

$^1$H-NMR (TMS, CDCl$_3$), δppm: 1.23 (d, 6.8 Hz, 3H), 1.25 (d, 6.8 Hz, 3H), 1.90 (s, 3H), 3.71 (q, 6.8 Hz, 1H), 3.74 (q, 6.8 Hz, 1H), 6.93 (Ar—H, 2H), 7.12-7.32 (Ar—H, 7H).

Step (b), Hydrogenolysis

To 2.7 ml of methanol, 0.70 g (2.72 mmol, 1 eq.) of the above purified product of the optically active tertiary amine, 0.81 g (13.49 mmol, 4.96 eq.) of acetic acid, and 34.8 mg (0.124 wt % Pd, based on the total weight of the tertiary amine) of a palladium catalyst (having 5% palladium carried on an activated carbon containing 50 wt % of water) were added. The hydrogen pressure was adjusted to 0.6 MPa, and the stirring was conducted at 65° C. for 40 hr. After the reaction, the reaction liquid was filtrated using a filtration aid (CELITE (trade name)), concentrated, and vacuum-dried, thereby obtaining a crude product of an acetate of an optically active (S)-1-(4-fluorophenyl)ethylamine N-monomethyl, represented by the following formula.

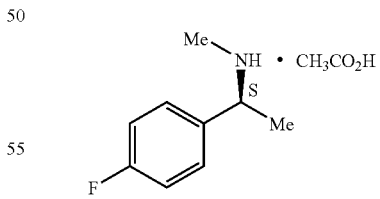

Then, 1N sodium hydroxide aqueous solution was added to the above crude product of the acetate to have a basic solution, followed by extraction with ethyl acetate. The recovered organic layer was dried with anhydrous sodium sulfate, followed by filtration, concentration, and vacuum drying, thereby obtaining 0.35 g of a crude product of an optically active (S)-1-(4-fluorophenyl)ethylamine N-monomethyl represented by the following formula.

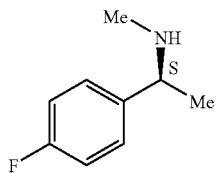

The yield was 83%. The above crude product was found by chiral gas chromatography to have a conversion of 99% and an enantiomeric excess of 99.3% ee. In terms of severing position selectivity whether the N—C* bond is severed at the broken line "a" to produce a compound A or at the broken line "b" to produce a compound B (i.e., the above optically active (S)-1-(4-fluorophenyl)ethylamine N-monomethyl) in the above formula 11, the above crude product was found by chiral gas chromatography to contain 1 part by mole of the compound A and 99 parts by mole of the compound B.

$^1$H-NMR (TMS, CDCl$_3$), δppm: 1.33 (d, 6.4 Hz, 3H), 1.65 (br, 1H), 2.29 (s, 3H), 3.64 (q, 6.4 Hz, 1H), 7.01 (Ar—H, 2H), 7.26 (Ar—H, 2H).

EXAMPLE 2

SYNTHESIS OF OPTICALLY ACTIVE (R)-1-(4-FLUOROPHENYL)ETHYLAMINE N-MONOMETHYL

Example 1 was repeated except in that (S)-1-phenylethylamine was replaced with (R)-1-phenylethylamine, thereby obtaining an optically active (R)-1-(4-fluorophenyl)ethylamine N-monomethyl.

NMR data of an optically active tertiary amine, represented by the following formula, are shown as follows.

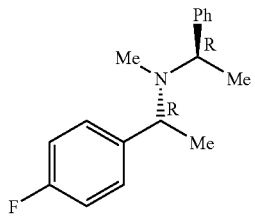

$^1$H-NMR (TMS, CDCl$_3$), δppm: 1.23 (d, 6.8 Hz, 3H), 1.25 (d, 6.8 Hz, 3H), 1.90 (s, 3H), 3.71 (q, 6.8 Hz, 1H), 3.74 (q, 6.8 Hz, 1H), 6.93 (Ar—H, 2H), 7.12-7.32 (Ar—H, 7H).

NMR data of an optically active (R)-1-(4-fluorophenyl)ethylamine N-monomethyl, represented by the following formula, are shown as follows.

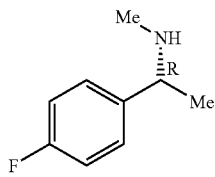

$^1$H-NMR (TMS, CDCl$_3$), δppm: 1.33 (d, 6.4 Hz, 3H), 1.65 (br, 1H), 2.29 (s, 3H), 3.64 (q, 6.4 Hz, 1H), 7.01 (Ar—H, 2H), 7.26 (Ar—H, 2H).

In chiral gas chromatography, the major enantiomer peaks of Example 2 were identical with the minor enantiomer peaks of Example 1, and the minor enantiomer peaks of Example 2 were identical with the major enantiomer peaks of Example 1.

EXAMPLE 3

OPTICALLY ACTIVE (S)-1-(4-FLUOROPHENYL)PROPYLAMINE N-MONOMETHYL

Step (c), Dehydration and Condensation

At first, 45.65 g (299.99 mmol, 1 eq.) of 4-fluorophenyl ethyl ketone, 39.99 g (330.00 mmol, 1.10 eq.) of (S)-1-phenylethylamine, and 3.27 g (23.99 mmol, 0.08 eq.) of zinc chloride were added to 300 ml of toluene. The resulting mixture was stirred for 42 hr under a heated reflux condition, while water (by-product) was removed from a Dean-Stark trap. The resulting reaction liquid was washed with 5% sodium hydroxide aqueous solution, 1.5N ammonium chloride aqueous solution, and water. The recovered organic layer was dried with anhydrous sodium sulfate, filtrated, concentrated and vacuum-dried, thereby obtaining 79.20 g of a crude product of an optically active imine represented by the following formula.

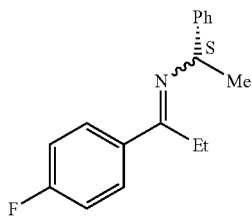

Conversion was found by gas chromatography to be 94%. The molecular ratio of E configuration to Z configuration of the crude product was found by 1H-NMR to be 75:25.

$^1$H-NMR (standard substance: TMS; solvent: CDCl$_3$) of E configuration, δppm: 1.05 (t, 7.8 Hz, 3H), 1.54 (d, 6.6 Hz, 3H), 2.73 (m, 2H), 4.87 (q, 6.6 Hz 1H), 6.90-7.90 (Ar—H, 9H).

$^1$H-NMR (standard substance: TMS; solvent: CDCl$_3$) of Z configuration, δppm: 1.09 (t, 7.6 Hz, 3H), 1.38 (d, 6.6 Hz, 3H), 2.56 (m, 2H), 4.36 (q, 6.6 Hz 1H), 6.90-7.90 (Ar—H, 9H).

Step (d), Asymmetric Reduction

At first, 79.20 g (299.99 mmol, 1 eq.) of the crude product of the optically active imine produced by the above step (c) were added to 390 ml of methanol. The resulting solution was cooled down to 0° C. Then, 11.35 g (300.03 mmol, 1.00 eq.) of sodium borohydride were added, followed by stirring for 3 hr at the same temperature. After the reaction, 1N hydrochloric acid aqueous solution was added to decompose the remaining sodium borohydride. Then, the reaction liquid was made basic by adding 1N sodium hydroxide aqueous solution, followed by extraction with toluene. The collected organic layer was washed with saturated brine and water, dried with anhydrous sodium sulfate, filtrated, concentrated, and vacuum-dried, thereby obtaining 77.50 g of a crude product of an optically active secondary amine represented by the following formula.

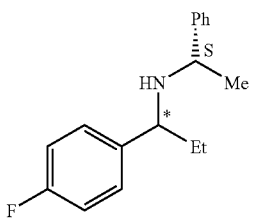

It was found by gas chromatography that conversion of the crude product was 100% and that the ratio of a diastereomer of S—S configuration to a diastereomer of R—S configuration was 68:32.

The NMR data of the crude product are as follows.

$^1$H-NMR (TMS, CDCl$_3$) of S—S configuration, δppm: 0.72 (t, 7.4 Hz, 3H), 1.25 (d, 6.4 Hz, 3H), 1.40-1.90 (m, 2H), 1.57 (br, 1H), 3.19 (t, 7.0 Hz, 1H), 3.44 (q, 6.4 Hz, 1H), 6.92-7.36 (Ar—H, 9H).

$^1$H-NMR (TMS, CDCl$_3$) of R—S configuration, δppm: 0.75 (t, 7.4 Hz, 3H), 1.33 (d, 6.4 Hz, 3H), 1.40-1.90 (m, 2H), 1.57 (br, 1H), 3.54 (dd, 5.2, 8.4 Hz, 1H), 3.68 (q, 6.4 Hz, 1H), 6.92-7.36 (Ar—H, 9H).

Step (a), Alkylation

At first, 5.00 g (19.35 mmol, 1 eq.) of the above crude product of the optically active secondary amine, 27.50 g (193.74 mmol, 10.01 eq.) of methyl iodide, and 5.36 g (38.78 mmol, 2.00 eq.) of anhydrous potassium carbonate were added to 19.4 ml of dimethylformamide, followed by stirring at 50° C. for 25 hr. After the reaction, the reaction liquid was diluted with ethyl acetate, followed by washing with 1N sodium hydroxide aqueous solution, drying with anhydrous sodium sulfate, filtration, concentration, and vacuum drying, thereby obtaining 5.46 g of a crude product of an optically active tertiary amine represented by the following formula.

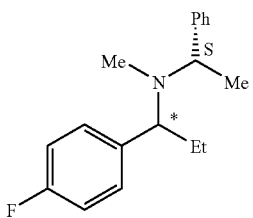

Conversion was found by gas chromatography to be 100%. Furthermore, the crude product was purified by a silica gel column chromatography (ethyl acetate:n-hexane=1:20), thereby obtaining 4.11 g of a purified product of the optically active tertiary amine. The total yield from the dehydration and condensation to the alkylation was 78%.

$^1$H-NMR (TMS, CDCl$_3$) of S—S configuration, δppm: 0.73 (t, 7.4 Hz, 3H), 1.25 (d, 6.4 Hz, 3H), 1.56-2.06 (m, 2H), 2.09 (s, 3H), 3.47 (dd, 6.0, 8.4 Hz, 1H), 3.64 (q, 6.4 Hz, 1H), 6.95-7.40 (Ar—H, 9H).

Step (b), Hydrogenolysis

To 3.7 ml of methanol, 1.00 g (3.69 mmol, 1 eq.) of the above purified product of the optically active tertiary amine, 1.11 g (18.48 mmol, 5.01 eq.) of acetic acid, and 50.0 mg (0.125 wt % in terms of Pd) of a palladium catalyst (having 5% palladium carried on an activated carbon containing 50 wt % of water) were added. The hydrogen pressure was adjusted to 0.5 MPa, and the stirring was conducted at 60° C. for 15 hr. After the reaction, the reaction liquid was filtrated using a filtration aid (CELITE (trade name)), concentrated, and vacuum-dried, thereby obtaining a crude product of an acetate of an optically active (S)-1-(4-fluorophenyl)propylamine N-monomethyl, represented by the following formula.

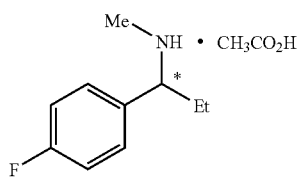

Then, 1N sodium hydroxide was added to the above crude product of the acetate to have a basic solution, followed by extraction with ethyl acetate. The recovered organic layer was dried with anhydrous sodium sulfate, followed by filtration, concentration, and vacuum drying, thereby obtaining 0.51 g of a crude product of an optically active (S)-1-(4-fluorophenyl)propylamine N-monomethyl represented by the following formula.

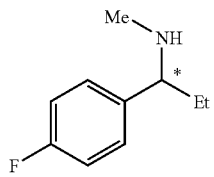

The yield was 82%. The above crude product was found by chiral gas chromatography to have a conversion of 100% and an enantiomeric excess of 36% ee. In terms of severing position selectivity whether the N—C* bond is severed at the broken line "a" to produce a compound A or at the broken line "b" to produce a compound B (i.e., the above optically active (S)-1-(4-fluorophenyl)propylamine N-monomethyl) in the above formula 11, the above crude product was found by chiral gas chromatography to contain 1 part by mole of the compound A and 99 parts by mole of the compound B.

$^1$H-NMR (TMS, CDCl$_3$), δppm: 0.79 (t, 7.4 Hz, 3H), 1.61 (m, 1H), 1.66 (br, 1H), 1.74 (m, 1H), 2.26 (s, 3H), 3.35 (dd, 5.6, 8.0 Hz, 1H), 7.00 (Ar—H, 2H), 7.23 (Ar—H, 2H).

EXAMPLE 4

SYNTHESIS OF OPTICALLY ACTIVE (R)-1-(4-FLUOROPHENYL)PROPYLAMINE N-MONOMETHYL

Example 3 was repeated except in that (S)-1-phenylethylamine was replaced in the step (c) with (R)-1-phenylethylamine, thereby obtaining an optically active (R)-1-(4-fluorophenyl)propylamine N-monomethyl.

NMR data of an optically active tertiary amine, represented by the following formula, are shown in the following.

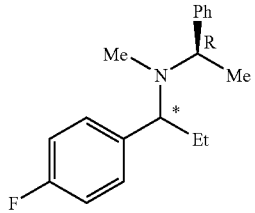

¹H-NMR (TMS, CDCl₃) of R—R configuration, δppm: 0.73 (t, 7.4 Hz, 3H), 1.25 (d, 6.4 Hz, 3H), 1.56-2.06 (m, 2H), 2.09 (s, 3H), 3.47 (dd, 6.0, 8.4 Hz, 1H), 3.64 (q, 6.4 Hz, 1H), 6.95-7.40 (Ar—H, 9H).

NMR data of an optically active (R)-1-(4-fluorophenyl) propylamine N-monomethyl, represented by the following formula, are shown as follows.

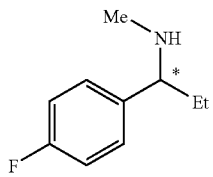

¹H-NMR (TMS, CDCl₃), δppm: 0.79 (t, 7.4 Hz, 3H), 1.61 (m, 1H), 1.66 (br, 1H), 1.74 (m, 1H), 2.26 (s, 3H), 3.35 (dd, 5.6, 8.0 Hz, 1H), 7.00 (Ar—H, 2H), 7.23 (Ar—H, 2H).

In chiral gas chromatography, the major enantiomer peaks of Example 4 were identical with the minor enantiomer peaks of Example 3, and the minor enantiomer peaks of Example 4 were identical with the major enantiomer peaks of Example 3.

EXAMPLE 5

SYNTHESIS OF OPTICALLY ACTIVE (S)-1-(4-TRIFLUOROMETHYLPHENYL)ETHYLAMINE N-MONOMETHYL

Step (c), Dehydration and Condensation

At first, 5.02 g (26.68 mmol, 1 eq.) of 4-trifluoromethylphenyl methyl ketone, 3.67 g (30.29 mmol, 1.14 eq.) of (S)-1-phenylethylamine, and 0.11 g (0.81 mmol, 0.03 eq.) of zinc chloride were added to 27 ml of toluene. The resulting mixture was stirred for 15 hr under a heated reflux condition, while water (by-product) was removed from a Dean-Stark trap. The resulting reaction liquid was washed with 5% sodium hydroxide aqueous solution, 1.5N ammonium chloride aqueous solution, and water. The recovered organic layer was dried with anhydrous sodium sulfate, filtrated, concentrated and vacuum-dried, thereby obtaining 8.20 g of a crude product of an optically active imine represented by the following formula.

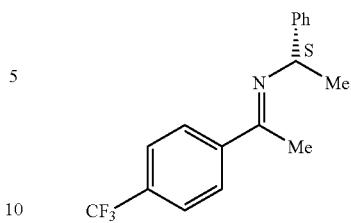

Conversion was found by gas chromatography to be 99%.

¹H-NMR (TMS; CDCl₃), δppm: 1.54 (d, 6.6 Hz, 3H), 2.29 (s, 3H), 4.85 (q, 6.6 Hz, 1H), 7.24 (Ar—H, 1H), 7.34 (Ar—H, 2H), 7.46 (Ar—H, 2H), 7.63 (Ar—H, 2H), 7.94 (Ar—H, 2H).

Step (d), Asymmetric Reduction

At first, 8.20 g (26.68 mmol, 1 eq.) of the crude product of the optically active imine produced by the above step (c) were added to 22 ml of methanol. The resulting solution was cooled down to 0° C. Then, 1.06 g (28.02 mmol, 1.05 eq.) of sodium borohydride were added, followed by stirring for 5.5 hr at the same temperature. After the reaction, 1N hydrochloric acid aqueous solution was added to decompose the remaining sodium borohydride. Then, the reaction liquid was made basic by adding 1N sodium hydroxide aqueous solution, followed by extraction with toluene. The collected organic layer was washed with water, dried with anhydrous sodium sulfate, filtrated, concentrated, and vacuum-dried, thereby obtaining 7.91 g of a crude product of an optically active secondary amine represented by the following formula.

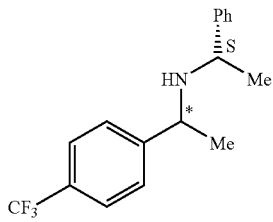

It was found by gas chromatography that conversion of the crude product was 100% and that the ratio of a diastereomer of S—S configuration to a diastereomer of R—S configuration was 84:16.

¹H-NMR (TMS, CDCl₃) of S—S configuration, δppm: 1.27 (d, 6.6 Hz, 3H), 1.29 (d, 6.6 Hz, 3H), 1.59 (br, 1H), 3.45 (q, 6.6 Hz, 1H), 3.57 (q, 6.6 Hz, 1H), 7.12-7.67 (Ar—H, 9H).

¹H-NMR (TMS, CDCl₃) of R—S configuration, δppm: 1.37 (d, 6.8 Hz, 6H), 1.59 (br, 1H), 3.76 (q, 6.8 Hz, 1H), 3.84 (q, 6.8 Hz, 1H), 7.12-7.67 (Ar—H, 9H)

Steps (e) and (f), Salt Formation and its Recrystallization 3.00 g (10.12 mmol, 1 eq.) of the crude product of the optically active secondary amine produced by the above step (d) and 1.68 g (10.11 mmol, 1.00 eq.) of phthalic acid were added to 10.5 ml of i-propanol, followed by stirring at 70° C. for 40 min. Then, 15 ml of n-hexane were added, followed by allowing it to cool down to room temperature and then allowing it to stand still for 12 hr. The precipitated crystals were filtered, washed with a small amount of n-hexane, and vacuum-dried, thereby obtaining 3.74 g of crystals of a phthalate of the optically active secondary amine, which is represented by the following formula.

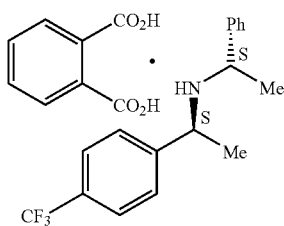

The diastereomeric excess of the crystals was determined by gas chromatography in a manner that the phthalate was turned into a free base with 0.5N sodium hydroxide aqueous solution. The result was 94.2% de. Furthermore, 3.60 g of the above crystals of the phthalate were added to 9 ml of i-propanol, followed by stirring at 70° C. for 40 min, adding 6 ml of n-hexane, allowing it to cool down to room temperature, and allowing it to stand still for 12 hr. The precipitated crystals were filtrated, followed by washing with a small amount of n-hexane and vacuum drying, thereby obtaining 3.30 g of crystals of the above phthalate of the optically active secondary amine. The diastereomeric excess of the crystals was determined by gas chromatography in a manner that the phthalate was turned into a free base with 0.5N sodium hydroxide aqueous solution. The result was 99.1% de. The total yield from the dehydration and the condensation to the salt formation and its recrystallization was 74%.

$^1$H-NMR (TMS, CDCl$_3$), δppm: 1.80 (d, 6.8 Hz, 6H), 4.04 (q, 6.8 Hz, 1H), 4.13 (q, 6.8 Hz, 1H), 7.35-7.73 (Ar—H, 11H), 8.45-8.55 (Ar—H, 2H), 10.60 (br, 3H).

Then, 0.5N sodium hydroxide aqueous solution was added to 3.00 g (6.53 mmol) of the crystals of the phthalate to have a basic solution, followed by extraction with toluene. The collected organic layer was washed with saturated brine, dried with anhydrous sodium sulfate, filtrated, concentrated, and vacuum-dried, thereby obtaining 1.92 g of a purified product of an optically active secondary amine represented by the following formula.

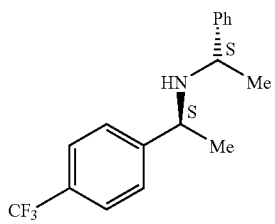

The recovery was quantitative.

$^1$H-NMR (TMS, CDCl$_3$), δppm: 1.27 (d, 6.6 Hz, 3H), 1.29 (d, 6.6 Hz, 3H), 1.59 (br, 1H), 3.45 (q, 6.6 Hz, 1H), 3.57 (q, 6.6 Hz, 1H), 7.12-7.67 (Ar—H, 9H).

Step (a), Alkylation

At first, 0.80 g (2.73 mmol, 1 eq.) of the above purified product of the optically active secondary amine, 3.88 g (27.34 mmol, 10.01 eq.) of methyl iodide, and 0.75 g (5.43 mmol, 1.99 eq.) of anhydrous potassium carbonate were added to 2.7 ml of dimethylformamide, followed by stirring at room temperature for 17 hr. After the reaction, the reaction liquid was diluted with a mixed solution of ethyl acetate and n-hexane (ethyl acetate:n-hexane=1:10), followed by washing with water, 1N sodium hydroxide aqueous solution and saturated brine, drying with anhydrous sodium sulfate, filtration, concentration, and vacuum drying, thereby obtaining 0.98 g of a crude product of an optically active tertiary amine represented by the following formula.

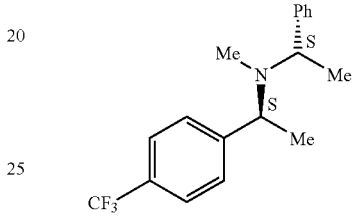

Conversion was found by gas chromatography to be 98%. Furthermore, the crude product was purified by a silica gel column chromatography (n-hexane), thereby obtaining 0.62 g of a purified product of the optically active tertiary amine. The yield was 74%.

$^1$H-NMR (TMS, CDCl$_3$), δppm: 1.33 (d, 6.8 Hz, 3H), 1.35 (d, 6.8 Hz, 3H), 1.98 (s, 3H), 3.81 (q, 6.8 Hz, 1H), 3.88 (q, 6.8 Hz, 1H), 7.20-7.63 (Ar—H, 9H).

Step (b), Hydrogenolysis

To 1.6 ml of methanol, 0.50 g (1.63 mmol, 1 eq.) of the above purified product of the optically active tertiary amine, 0.49 g (8.16 mmol, 5.01 eq.) of acetic acid, and 24.9 mg (0.125 wt % Pd) of a palladium catalyst (having 5% palladium carried on an activated carbon containing 50 wt % of water) were added. The hydrogen pressure was adjusted to 0.5 MPa, and the stirring was conducted at 60° C. for 13.5 hr. After the reaction, the reaction liquid was filtered using a filtration aid (CELITE (trade name)), concentrated, and vacuum-dried, thereby obtaining a crude product of an acetate of an optically active (S)-1-(4-trifluoromethylphenyl)ethylamine N-monomethyl, represented by the following formula.

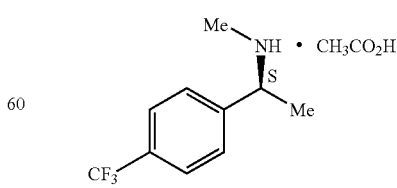

Then, 1N sodium hydroxide aqueous solution was added to the above crude product of the acetate to have a basic solution, followed by extraction with ethyl acetate. The recovered organic layer was dried with anhydrous sodium sulfate, followed by filtration, concentration, and vacuum drying, thereby obtaining 0.31 g of a crude product of an optically active (S)-1-(4-trifluoromethylphenyl)ethylamine N-monomethyl represented by the following formula.

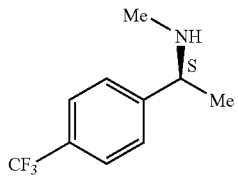

The yield was 94%. The above crude product was found by chiral gas chromatography to have a conversion of 100% and an enantiomeric excess of 99.1% ee. In terms of severing position selectivity whether the N—C* bond is severed at the broken line "a" to produce a compound A or at the broken line "b" to produce a compound B (i.e., the above optically active (S)-1-(4-trifluoromethylphenyl)ethylamine N-monomethyl) in the above formula 11, the above crude product was found by chiral gas chromatography to contain 1 part by mole of the compound A and 100 parts by mole of the compound B.

$^1$H-NMR (TMS, CDCl$_3$), δppm: 1.51 (d, 6.8 Hz, 3H), 2.35 (s, 3H), 3.88 (q, 6.8 Hz, 1H), 5.16 (br, 1H), 7.54 (Ar—H, 2H), 7.63 (Ar—H, 2H).

EXAMPLE 6

SYNTHESIS OF OPTICALLY ACTIVE (R)-1-(4-TRIFLUOROMETHYLPHENYL) ETHYLAMINE N-MONOMETHYL

Example 5 was repeated except in that (S)-1-phenylethylamine was replaced in the step (c) with (R)-1-phenylethylamine, thereby obtaining an optically active (R)-1-(4-trifluoromethylphenyl)ethylamine N-monomethyl.

NMR data of an optically active tertiary amine, represented by the following formula, are shown as follows.

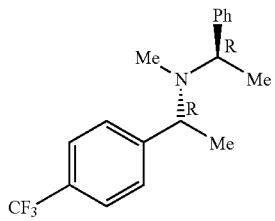

$^1$H-NMR (TMS, CDCl$_3$), δppm: 1.33 (d, 6.8 Hz, 3H), 1.35 (d, 6.8 Hz, 3H), 1.98 (s, 3H), 3.81 (q, 6.8 Hz, 1H), 3.88 (q, 6.8 Hz, 1H), 7.20-7.63 (Ar—H, 9H).

NMR data of an optically active (R)-1-(4-trifluoromethylphenyl)ethylamine N-monomethyl, represented by the following formula, are shown as follows.

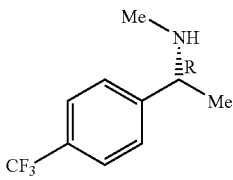

$^1$H-NMR (TMS, CDCl$_3$), δppm: 1.51 (d, 6.8 Hz, 3H), 2.35 (s, 3H), 3.88 (q, 6.8 Hz, 1H), 5.16 (br, 1H), 7.54 (Ar—H, 2H), 7.63 (Ar—H, 2H).

In chiral gas chromatography, the major enantiomer peaks of Example 6 were identical with the minor enantiomer peaks of Example 5, and the minor enantiomer peaks of Example 6 were identical with the major enantiomer peaks of Example 5.

EXAMPLE 7

SYNTHESIS OF OPTICALLY ACTIVE (S)-1-(4-TRIFLUOROMETHYLPHENYL) ETHYLAMINE N-MONOETHYL

Step (a), Alkylation

At first, (a) 0.80 g (2.73 mmol, 1 eq.) of the purified product of the optically active secondary amine, produced by the "salt formation and its recrystallization" of Example 5, (b) 8.51 g (54.56 mmol, 19.99 eq.) of ethyl iodide, and (c) 0.75 g (5.43 mmol, 1.99 eq.) of anhydrous potassium carbonate were added to 2.7 ml of dimethylformamide, followed by stirring at 100° C. for 21 hr. After the reaction, the reaction liquid was diluted with ethyl acetate, followed by washing with 1N sodium hydroxide aqueous solution and saturated brine, drying with anhydrous sodium sulfate, filtration, concentration, and vacuum drying, thereby obtaining 0.82 g of a crude product of an optically active tertiary amine represented by the following formula.

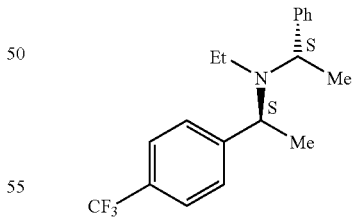

Conversion was found by gas chromatography to be 99%. Furthermore, the crude product was purified by a silica gel column chromatography (ethyl acetate:n-hexane=1:20), thereby obtaining 0.77 g of a purified product of the optically active tertiary amine. The yield was 88%.

$^1$H-NMR (TMS, CDCl$_3$), δppm: 0.83 (t, 7.0 Hz, 3H), 1.39 (d, 6.8 Hz, 3H), 1.40 (d, 6.8 Hz, 3H), 2.49 (m, 1H), 2.68 (m, 1H), 4.02 (m, 2H), 7.17-7.57 (Ar—H, 9H).

Step (b), Hydrogenolysis

To 2.2 ml of methanol, 0.70 g (2.18 mmol, 1 eq.) of the above purified product of the optically active tertiary amine, 0.65 g (10.82 mmol, 4.96 eq.) of acetic acid, and 35.0 mg (0.125 wt % Pd) of a palladium catalyst (having 5% palladium carried on an activated carbon containing 50 wt % of water) were added. The hydrogen pressure was adjusted to 0.5 MPa, and the stirring was conducted at 60° C. for 17 hr. After the reaction, the reaction liquid was filtrated using a filtration aid (CELITE (trade name)), concentrated, and vacuum-dried, thereby obtaining a crude product of an acetate of an optically active (S)-1-(4-trifluoromethylphenyl)ethylamine N-monoethyl, represented by the following formula.

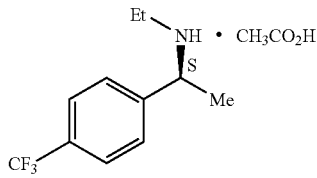

Then, 1N sodium hydroxide aqueous solution was added to the above crude product of the acetate to have a basic solution, followed by extraction with ethyl acetate. The recovered organic layer was dried with anhydrous sodium sulfate, followed by filtration, concentration, and vacuum drying, thereby obtaining 0.42 g of a crude product of an optically active (S)-1-(4-trifluoromethylphenyl)ethylamine N-monoethyl represented by the following formula.

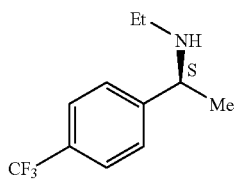

The yield was 89%. The above crude product was found by chiral gas chromatography to have a conversion of 100% and an enantiomeric excess of 99.1% ee. In terms of severing position selectivity whether the N—C* bond is severed at the broken line "a" to produce a compound A or at the broken line "b" to produce a compound B (i.e., the above optically active (S)-1-(4-trifluoromethylphenyl)ethylamine N-monoethyl) in the above formula 11, the above crude product was found by chiral gas chromatography to contain 1 part by mole of the compound A and 99 parts by mole of the compound B.

$^1$H-NMR (TMS, CDCl$_3$), δppm: 1.08 (t, 7.2 Hz, 3H), 1.35 (d, 6.8 Hz, 3H), 1.35 (br, 1H), 2.38-2.60 (m, 2H), 3.85 (q, 6.8 Hz, 1H), 7.44 (Ar—H, 2H), 7.58 (Ar—H, 2H).

EXAMPLE 8

SYNTHESIS OF OPTICALLY ACTIVE (R)-1-(4-TRIFLUOROMETHYLPHENYL) ETHYLAMINE N-MONOETHYL

Example 7 was repeated except in that the purified product of the optically active secondary amine, produced by the "salt formation and its recrystallization" of Example 5, was replaced with that of Example 6, thereby obtaining an optically active (R)-1-(4-trifluoromethylphenyl)ethylamine N-monoethyl.

NMR data of an optically active tertiary amine, represented by the following formula, are shown as follows.

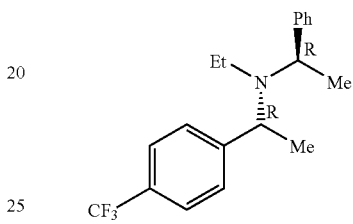

$^1$H-NMR (TMS, CDCl$_3$), δppm: 0.83 (t, 7.0 Hz, 3H), 1.39 (d, 6.8 Hz, 3H), 1.40 (d, 6.8 Hz, 3H), 2.49 (m, 1H), 2.68 (m, 1H), 4.02 (m, 2H), 7.17-7.57 (Ar—H, 9H).

NMR data of an optically active (R)-1-(4-trifluoromethylphenyl)ethylamine N-monoethyl, represented by the following formula, are shown as follows.

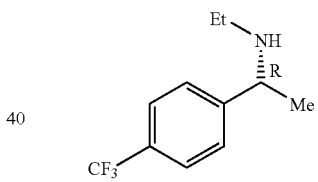

$^1$H-NMR (TMS, CDCl$_3$), δppm: 1.08 (t, 7.2 Hz, 3H), 1.35 (d, 6.8 Hz, 3H), 1.35 (br, 1H), 2.38-2.60 (m, 2H), 3.85 (q, 6.8 Hz, 1H), 7.44 (Ar—H, 2H), 7.58 (Ar—H, 2H).

EXAMPLE 9

SYNTHESIS OF OPTICALLY ACTIVE (S)-1-(3,5-BIS(TRIFLUOROMETHYL)PHENYL) ETHYLAMINE N-MONOMETHYL

Step (c), Dehydration and Condensation

At first, 10.00 g (39.04 mmol, 1 eq.) of 3,5-bis(trifluoromethyl)phenyl methyl ketone, 4.96 g (40.93 mmol, 1.05 eq.) of (S)-1-phenylethylamine, and 0.37 g (1.95 mmol, 0.05 eq.) of p-toluenesulfonic acid monohydrate were added to 100 ml of toluene. The resulting mixture was stirred for 24 hr under a heated reflux condition, while water (by-product) was removed from a Dean-Stark trap. The resulting reaction liquid was washed with a saturated sodium hydrogencarbonate aqueous solution. The recovered organic layer was dried with anhydrous magnesium sulfate, filtrated, concentrated and vacuum-dried, thereby obtaining 14.34 g of a crude product of an optically active imine represented by the following formula.

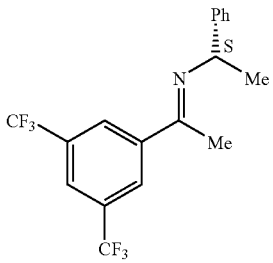

The yield was quantitative.

$^1$H-NMR (TMS; CDCl$_3$), δppm: 1.55 (d, 6.4 Hz, 3H), 2.33 (s, 3H), 4.87 (q, 6.4 Hz, 1H), 7.24 (Ar—H, 1H), 7.35 (Ar—H, 2H), 7.45 (Ar—H, 2H), 8.31 (Ar—H, 1H), 8.38 (Ar—H, 2H).

Step (d), Asymmetric Reduction

At first, 14.34 g (39.04 mmol, 1 eq.) of the crude product of the optically active imine produced by the above step (c) were added to 156 ml of methanol. The resulting solution was cooled down to 0° C. Then, 1.48 g (39.12 mmol, 1.00 eq.) of sodium borohydride were added, followed by stirring for 5 hr at the same temperature. After the reaction, 1N hydrochloric acid aqueous solution was added to decompose the remaining sodium borohydride. Then, the reaction liquid was made basic by adding 1N sodium hydroxide aqueous solution, followed by extraction with toluene. The collected organic layer was washed with water, dried with anhydrous sodium sulfate, filtrated, concentrated, and vacuum-dried, thereby obtaining 14.31 g of a crude product of an optically active secondary amine represented by the following formula.

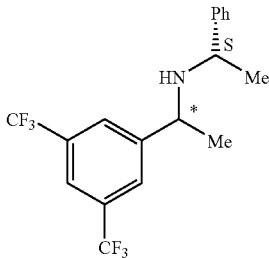

It was found by gas chromatography that conversion of the crude product was 100% and that the ratio of a diastereomer of S—S configuration to a diastereomer of R—S configuration was 84:16.

$^1$H-NMR (TMS, CDCl$_3$) of S—S configuration, δppm: 1.28 (d, 6.5 Hz, 3H), 1.29 (d, 6.4 Hz, 3H), 1.58 (br, 1H), 3.39 (q, 6.5 Hz, 1H), 3.65 (q, 6.4 Hz, 1H), 7.05-7.44 (Ar—H, 5H), 7.70 (Ar—H, 2H), 7.76 (Ar—H, 1H).

$^1$H-NMR (TMS, CDCl$_3$) of R—S configuration, δppm: 1.37 (d, 6.5 Hz, 3H), 1.38 (d, 6.5 Hz, 3H), 1.52 (br, 1H), 3.78 (q, 6.5 Hz, 1H), 3.87 (q, 6.5 Hz, 1H), 7.10-7.33 (Ar—H, 5H), 7.65 (Ar—H, 1H), 7.67 (Ar—H, 2H).

Steps (e) and (f), Salt Formation and its Recrystallization 14.31 g (39.04 mmol, 1 eq.) of the crude product of the optically active secondary amine produced by the above step (d) and 7.43 g (39.06 mmol, 1.00 eq.) of p-toluenesulfonic acid monohydrate were added to 23.4 ml of i-propanol, followed by stirring at 60° C. for 40 min. Then, 28.1 ml of n-heptane were added, followed by allowing it to cool down to room temperature and then stirring for 12 hr. The precipitated crystals were filtered, washed with a small amount of n-heptane, and vacuum-dried, thereby obtaining 10.90 g of crystals of a p-toluenesulfonate of the optically active secondary amine, which is represented by the following formula.

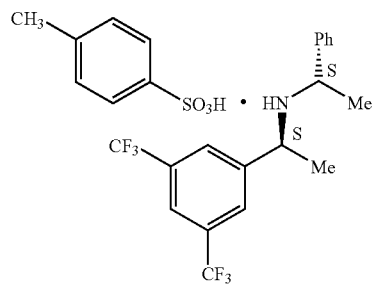

The diastereomeric excess of the crystals was determined by gas chromatography in a manner that the p-toluenesulfonate was turned into a free base with 1N sodium hydroxide aqueous solution. The result was 99.7% de. The total yield from the dehydration and the condensation to the salt formation and its recrystallization was 52%.

$^1$H-NMR (TMS, DMSO-d$_6$), δppm: 1.55 (d, 6.0 Hz, 3H), 1.58 (d, 6.0 Hz, 3H), 2.28 (s, 3H), 4.29 (q, 6.0 Hz, 1H), 4.54 (q, 6.0 Hz, 1H), 7.11 (Ar—H, 2H), 7.38 (Ar—H, 2H), 7.43 (Ar—H, 3H), 7.47 (Ar—H, 2H), 8.10 (Ar—H, 2H), 8.20 (Ar—H, 1H), 9.41 (br, 2H).

Then, 1N sodium hydroxide aqueous solution was added to 8.00 g (14.99 mmol) of the crystals of the p-toluenesulfonate to have a basic solution, followed by extraction with toluene. The collected organic layer was washed with saturated brine, dried with anhydrous sodium sulfate, filtrated, concentrated, and vacuum-dried, thereby obtaining 5.42 g of a purified product of an optically active secondary amine represented by the following formula.

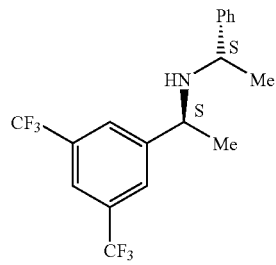

The recovery was quantitative.

$^1$H-NMR (TMS, CDCl$_3$), δppm: 1.28 (d, 6.5 Hz, 3H), 1.29 (d, 6.4 Hz, 3H), 1.58 (br, 1H), 3.39 (q, 6.5 Hz, 1H), 3.65 (q, 6.4 Hz, 1H), 7.05-7.44 (Ar—H, 5H), 7.70 (Ar—H, 2H), 7.76 (Ar—H, 1H).

Step (a), Alkylation

At first, 3.78 g (10.46 mmol, 1 eq.) of the above purified product of the optically active secondary amine, 2.96 g (20.85 mmol, 1.99 eq.) of methyl iodide, and 2.89 g (20.91 mmol, 2.00 eq.) of anhydrous potassium carbonate were added to a mixed solution of 2.6 ml of dimethylformamide and 7.8 ml of tetrahydrofuran, followed by stirring at 58° C. for 43 hr. After the reaction, the reaction liquid was diluted with ethyl acetate, followed by washing with saturated brine, drying with anhydrous sodium sulfate, filtration, concentration, and vacuum drying, thereby obtaining 5.72 g of a crude product of an optically active tertiary amine represented by the following formula.

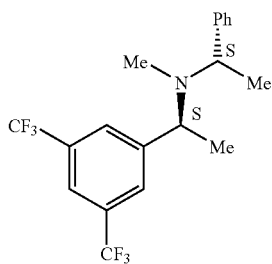

Conversion was found by gas chromatography to be 94%. Furthermore, the crude product was purified by a silica gel column chromatography (ethyl acetate:n-hexane=1:10), thereby obtaining 3.50 g of a purified product of the optically active tertiary amine. The yield was 89%.

$^1$H-NMR (TMS, CDCl$_3$), δppm: 1.37 (d, 6.8 Hz, 3H), 1.38 (d, 6.8 Hz, 3H), 2.00 (s, 3H), 3.76 (q, 6.8 Hz, 1H), 4.00 (q, 6.8 Hz, 1H), 7.20-7.40 (Ar—H, 5H), 7.76 (Ar—H, 1H), 7.82 (Ar—H, 2H).

Step (b), Hydrogenolysis

To 8.0 ml of methanol, 3.00 g (7.99 mmol, 1 eq.) of the above purified product of the optically active tertiary amine and 60.0 mg (0.05 wt % Pd) of a palladium catalyst (having 5% palladium carried on an activated carbon containing 50 wt % of water) were added. The hydrogen pressure was adjusted to 0.5 MPa, and the stirring was conducted at 60° C. for 21 hr. After the reaction, the reaction liquid was filtrated using a filtration aid (CELITE (trade name)), concentrated, and vacuum-dried, thereby obtaining 2.04 g of a crude product of an optically active (S)-1-(3,5-bis(trifluoromethyl)phenyl)ethylamine N-monomethyl, represented by the following formula.

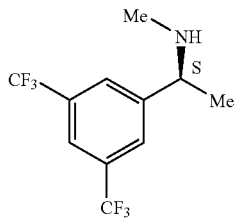

The above crude product was found by chiral gas chromatography to have a conversion of 97% and an enantiomeric excess of 99.7% ee. In terms of severing position selectivity whether the N—C* bond is severed at the broken line "a" to produce a compound A or at the broken line "b" to produce a compound B (i.e., the above optically active (S)-1-(3,5-bis(trifluoromethyl)phenyl)ethylamine N-monomethyl) in the above formula 11, the above crude product was found by chiral gas chromatography to contain 1 part by mole of the compound A and 99 parts by mole of the compound B. Furthermore, the above crude product was purified by a distillation, thereby obtaining 1.58 g of a purified product of the optically active (S)-1-(3,5-(bis(trifluoromethyl)phenyl)ethylamine N-monomethyl. The yield was 73%.

Boiling Point: 90-95° C./1070 Pa.

[α]$^{25}_D$: −34.7. $^1$H-NMR (TMS, CDCl$_3$), δppm: 1.38 (d, 6.4 Hz, 3H), 1.45 (br, 1H), 2.30 (s, 3H), 3.81 (q, 6.4 Hz, 1H), 7.75 (Ar—H, 1H), 7.80 (Ar—H, 2H).

EXAMPLE 10

SYNTHESIS OF OPTICALLY ACTIVE (R)-1-(3,5-BIS(TRIFLUOROMETHYL)PHENYL) ETHYLAMINE N-MONOMETHYL

Example 9 was repeated except in that (S)-1-phenylethylamine was replaced in the step (c) with (R)-1-phenylethylamine, thereby obtaining an optically active (R)-1-(3,5-bis(trifluoromethyl)phenyl)ethylamine N-monomethyl.

NMR data of an optically active tertiary amine, represented by the following formula, are shown as follows.

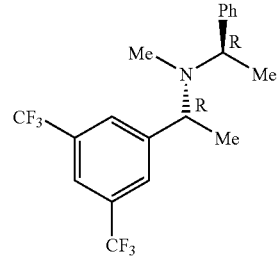

$^1$H-NMR (TMS, CDCl$_3$), δppm: 1.37 (d, 6.8 Hz, 3H), 1.38 (d, 6.8 Hz, 3H), 2.00 (s, 3H), 3.76 (q, 6.8 Hz, 1H), 4.00 (q, 6.8 Hz, 1H), 7.20-7.40 (Ar—H, 5H), 7.76 (Ar—H, 1H), 7.82 (Ar—H, 2H).

NMR data of an optically active (R)-1-(3,5-bis(trifluoromethyl)phenyl)ethylamine N-monomethyl, represented by the following formula, are shown as follows.

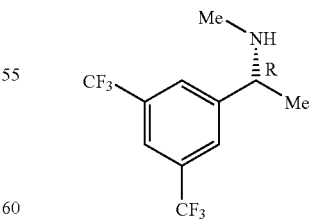

$^1$H-NMR (TMS, CDCl$_3$), δppm: 1.38 (d, 6.4 Hz, 3H), 1.45 (br, 1H), 2.30 (s, 3H), 3.81 (q, 6.4 Hz, 1H), 7.75 (Ar—H, 1H), 7.80 (Ar—H, 2H).

In chiral gas chromatography, the major enantiomer peaks of Example 10 were identical with the minor enantiomer peaks of Example 9, and the minor enantiomer peaks of Example 10 were identical with the major enantiomer peaks of Example 9.

EXAMPLE 11

SYNTHESIS OF OPTICALLY ACTIVE (R)-1-(3,5-BIS(TRIFLUOROMETHYL)PHENYL) ETHYLAMINE N-MONOMETHYL

Steps (e) and (f), Salt Formation and its Recrystallization

The mother liquor obtained by the "salt formation and its recrystallization" of Example 9 was concentrated, followed by adding 1N sodium hydroxide aqueous solution to have basicity and then extraction with toluene. The collected organic layer was washed with saturated brine, followed by drying with anhydrous sodium sulfate, filtration, concentration and vacuum drying, thereby obtaining 6.97 g of an optically active secondary amine (recovered from the above mother liquor) represented by the following formula.

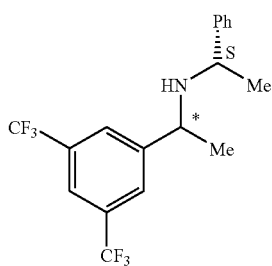

The recovery was quantitative. It was found by gas chromatography that the ratio of a diastereomer of S—S configuration to a diastereomer of R—S configuration of the secondary amine was 67:33. The total amount of 6.97 g (18.61 mmol, 1 eq.) of the secondary amine and 1.08 g (9.30 mmol, 0.50 eq.) of fumaric acid were added to a mixed solution of 2.2 ml of i-propanol and 22.3 ml of n-heptane, followed by stirring at 80° C. for 2 hr, then allowing it to cool down to room temperature, and then stirring for 12 hr at room temperature. The precipitated crystals were filtered, washed with a small amount of n-heptane, and vacuum-dried, thereby obtaining 2.02 g of crystals of a fumarate of the optically active secondary amine, which is represented by the following formula.

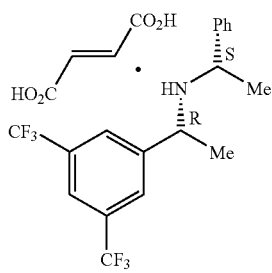

The diastereomeric excess of the crystals was determined by gas chromatography in a manner that the fumarate was turned into a free base with 1N sodium hydroxide aqueous solution. The result was 98.5% de. Furthermore, 2.00 g of the above fumarate were added to 7.3 ml of i-propanol, followed by dissolution at 80° C., allowing it to cool down to room temperature and stirring for 12 hr. The precipitated crystals were filtered, washed with a small amount of n-heptane, and vacuum-dried, thereby obtaining 1.72 g of crystals of a fumarate of the optically active secondary amine, which is represented by the above formula. The diastereomeric excess of the crystals was determined by gas chromatography in a manner that the fumarate was turned into a free base with 1N sodium hydroxide aqueous solution. The result was 100% de. The recovery of the fumarate of the optically active secondary amine (R—S configuration) from the mother liquor obtained by the "salt formation and its recrystallization of Example 9" was 59%.

$^1$H-NMR (standard substance: TMS; solvent: DMSO-$d_6$), δppm: 1.26 (d, 6.6 Hz, 3H), 1.29 (d, 6.6 Hz, 3H), 3.49 (br, 3H), 3.67 (q, 6.6 Hz, 1H), 3.93 (q, 6.6 Hz, 1H), 6.60 (s, 2H), 7.00-7.25 (Ar—H, 5H), 7.81 (Ar—H, 1H), 7.93 (Ar—H, 2H).

Then, 1N sodium hydroxide aqueous solution was added to 1.70 g (3.56 mmol) of the crystals (100% de) of the fumarate to have a basic solution, followed by extraction with toluene. The collected organic layer was washed with saturated brine, dried with anhydrous sodium sulfate, filtrated, concentrated, and vacuum-dried, thereby obtaining 1.29 g of a purified product of an optically active secondary amine represented by the following formula.

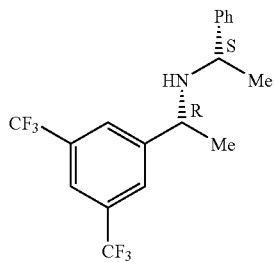

The recovery was quantitative.

$^1$H-NMR (TMS, CDCl$_3$), δppm: 1.37 (d, 6.5 Hz, 3H), 1.38 (d, 6.5 Hz, 3H), 1.52 (br, 1H), 3.78 (q, 6.5 Hz, 1H), 3.87 (q, 6.5 Hz, 1H), 7.10-7.33 (Ar—H, 5H), 7.65 (Ar—H, 1H), 7.67 (Ar—H, 2H).

Step (a), Alkylation

At first, 1.08 g (2.99 mmol, 1 eq.) of the above purified product (100% de) of the optically active secondary amine, 4.33 g (30.51 mmol, 10.20 eq.) of methyl iodide, and 0.83 g (6.01 mmol, 2.01 eq.) of anhydrous potassium carbonate were added to 3.0 ml of dimethylformamide, followed by stirring at room temperature for 18 hr. After the reaction, the reaction liquid was diluted with ethyl acetate, followed by washing with water and saturated brine, drying with anhydrous sodium sulfate, filtration, concentration, and vacuum drying, thereby obtaining 1.11 g of a crude product of an optically active tertiary amine represented by the following formula.

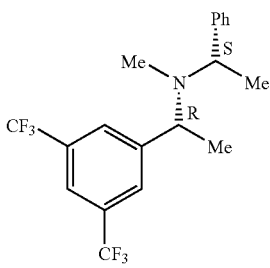

Conversion was found by gas chromatography to be 100%. Furthermore, the crude product was purified by a silica gel column chromatography (ethyl acetate:n-hexane=5:95), thereby obtaining 0.97 g of a purified product of the optically active tertiary amine. The yield was 87%.

$^1$H-NMR (TMS, CDCl$_3$), δppm: 1.33 (d, 6.8 Hz, 3H), 1.37 (d, 6.8 Hz, 3H), 2.12 (s, 3H), 3.73 (q, 6.8 Hz, 1H), 3.86 (q, 6.8 Hz, 1H), 7.20-7.43 (Ar—H, 5H), 7.72 (Ar—H, 1H), 7.87 (Ar—H, 2H).

Step (b), Hydrogenolysis

To 2.4 ml of methanol, 0.90 g (2.40 mmol, 1 eq.) of the above purified product of the optically active tertiary amine and 18.0 mg (0.05 wt % Pd) of a palladium catalyst (having 5% palladium carried on an activated carbon containing 50 wt % of water) were added. The hydrogen pressure was adjusted to 0.5 MPa, and the stirring was conducted at 60° C. for 17.5 hr. After the reaction, the reaction liquid was filtrated using a filtration aid (CELITE (trade name)), concentrated, and vacuum-dried, thereby obtaining 0.60 g of a crude product of an optically active (R)-1-(3,5-bis(trifluoromethyl)phenyl)ethylamine N-monomethyl, represented by the following formula.

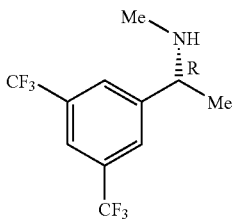

The yield was 92%. The above crude product was found by chiral gas chromatography to have a conversion of 100% and an enantiomeric excess of 100% ee. In terms of severing position selectivity whether the N—C* bond is severed at the broken line "a" to produce a compound A or at the broken line "b" to produce a compound B (i.e., the above optically active (R)-1-(3,5-bis(trifluoromethyl)phenyl)ethylamine N-monomethyl) in the above formula 11, the above crude product was found by chiral gas chromatography to contain 1 part by mole of the compound A and 99 parts by mole of the compound B.

$^1$H-NMR (TMS, CDCl$_3$), δppm: 1.38 (d, 6.4 Hz, 3H), 1.45 (br, 1H), 2.30 (s, 3H), 3.81 (q, 6.4 Hz, 1H), 7.75 (Ar—H, 1H), 7.80 (Ar—H, 2H).

EXAMPLE 12

SYNTHESIS OF OPTICALLY ACTIVE (S)-1-(3,5-BIS(TRIFLUOROMETHYL)PHENYL) ETHYLAMINE N-MONOMETHYL

Example 11 was repeated except in that the mother liquor obtained by the "salt formation and its recrystallization" of Example 9 was replaced with that of Example 10, thereby obtaining an optically active (S)-1-(3,5-bis(trifluoromethyl)phenyl)ethylamine N-monomethyl.

NMR data of an optically active tertiary amine, represented by the following formula, are shown as follows.

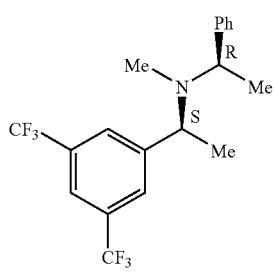

$^1$H-NMR (TMS, CDCl$_3$), δppm: 1.33 (d, 6.8 Hz, 3H), 1.37 (d, 6.8 Hz, 3H), 2.12 (s, 3H), 3.73 (q, 6.8 Hz, 1H), 3.86 (q, 6.8 Hz, 1H), 7.20-7.43 (Ar—H, 5H), 7.72 (Ar—H, 1H), 7.87 (Ar—H, 2H).

NMR data of an optically active (S)-1-(3,5-bis(trifluoromethyl)phenyl)ethylamine N-monomethyl, represented by the following formula, are shown as follows.

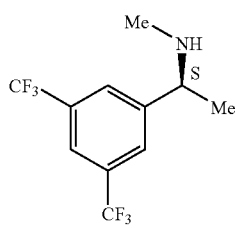

$^1$H-NMR (TMS, CDCl$_3$), δppm: 1.38 (d, 6.4 Hz, 3H), 1.45 (br, 1H), 2.30 (s, 3H), 3.81 (q, 6.4 Hz, 1H), 7.75 (Ar—H, 1H), 7.80 (Ar—H, 2H).

In chiral gas chromatography, the major enantiomer peaks of Example 12 were identical with the minor enantiomer peaks of Example 11, and the minor enantiomer peaks of Example 12 were identical with the major enantiomer peaks of Example 11.

EXAMPLE 13

SYNTHESIS OF OPTICALLY ACTIVE (S)-1-(3,5-BIS(TRIFLUOROMETHYL)PHENYL) ETHYLAMINE N-MONOETHYL

Step (a), Alkylation

At first, 1.50 g (4.15 mmol, 1 eq.) of the purified product of the optically active secondary amine produced by the "salt formation and its recrystallization" of Example 9, 9.71 g (62.26 mmol, 15.00 eq.) of ethyl iodide, and 1.15 g (8.32 mmol, 2.00 eq.) of anhydrous potassium carbonate were added to 4.2 ml of dimethylformamide, followed by stirring at 100° C. for 21 hr. After the reaction, the reaction liquid was diluted with a mixed solution of 1 part by volume of ethyl acetate and 1 part by volume of n-hexane, followed by washing with saturated brine, drying with anhydrous sodium sulfate, filtration, concentration, and vacuum drying, thereby obtaining 2.12 g of a crude product of an optically active tertiary amine represented by the following formula.

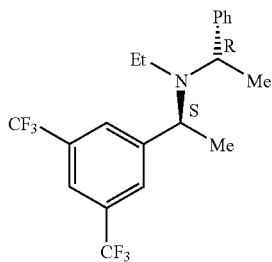

Conversion was found by gas chromatography to be 92%. Furthermore, the crude product was purified by a silica gel column chromatography (n-hexane), thereby obtaining 1.32 g of a purified product of the optically active tertiary amine. The yield was 81%.

$^1$H-NMR (TMS, CDCl$_3$), δppm: 0.89 (t, 7.2 Hz, 3H), 1.43 (d, 6.8 Hz, 3H), 1.45 (d, 6.8 Hz, 3H), 2.51 (m, 1H), 2.70 (m, 1H), 4.02 (q, 6.8 Hz, 1H), 4.08 (q, 6.8 Hz, 1H), 7.15-7.43 (Ar—H, 5H), 7.68 (Ar—H, 1H), 7.77 (Ar—H, 2H).

Step (b), Hydrogenolysis

To 1.7 ml of methanol, 0.66 g (1.70 mmol, 1 eq.) of the above purified product of the optically active tertiary amine, 0.83 g (13.82 mmol, 8.13 eq.) of acetic acid, and 53.3 mg (0.202 wt % Pd) of a palladium catalyst (having 5% palladium carried on an activated carbon containing 50 wt % of water) were added. The hydrogen pressure was adjusted to 0.5-0.6 MPa, and the stirring was conducted at 60-70° C. for 36 hr. After the reaction, the reaction liquid was filtrated using a filtration aid (CELITE (trade name)), concentrated, and vacuum-dried, thereby obtaining 0.43 g of a crude product of an optically active (S)-1-(3,5-bis(trifluoromethyl) phenyl)ethylamine N-monoethyl, represented by the following formula.

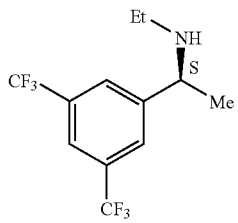

The yield was 90%. The above crude product was found by chiral gas chromatography to have a conversion of 100% and an enantiomeric excess of 99.7% ee. In terms of severing position selectivity whether the N—C* bond is severed at the broken line "a" to produce a compound A or at the broken line "b" to produce a compound B (i.e., the above optically active (S)-1-(3,5-bis(trifluoromethyl)phenyl)ethylamine N-monoethyl) in the above formula 11, the above crude product was found by chiral gas chromatography to contain 1 part by mole of the compound A and 99 parts by mole of the compound B.

$^1$H-NMR (TMS, CDCl$_3$), δppm: 1.09 (t, 7.2 Hz, 3H), 1.37 (d, 6.4 Hz, 3H), 1.40 (br, 1H), 2.36-2.49 (m, 1H), 2.49-2.63 (m, 1H), 3.92 (q, 6.4 Hz, 1H), 7.75 (Ar—H, 1H), 7.81 (Ar—H, 2H).

EXAMPLE 14

SYNTHESIS OF OPTICALLY ACTIVE (R)-1-(3,5-BIS(TRIFLUOROMETHYL)PHENYL) ETHYLAMINE N-MONOETHYL

Example 13 was repeated except in that the purified product of the optically active secondary amine produced by the "salt formation and its recrystallization" of Example 9 was replaced in the step (a) with that of Example 10, thereby obtaining an optically active (R)-1-(3,5-bis(trifluoromethyl) phenyl)ethylamine N-monoethyl.

NMR data of an optically active tertiary amine, represented by the following formula, are shown as follows.

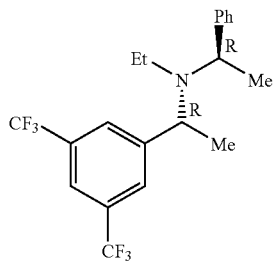

$^1$H-NMR (TMS, CDCl$_3$), δppm: 0.89 (t, 7.2 Hz, 3H), 1.43 (d, 6.8 Hz, 3H), 1.45 (d, 6.8 Hz, 3H), 2.51 (m, 1H), 2.70 (m, 1H), 4.02 (q, 6.8 Hz, 1H), 4.08 (q, 6.8 Hz, 1H), 7.15-7.43 (Ar—H, 5H), 7.68 (Ar—H, 1H), 7.77 (Ar—H, 2H).

NMR data of an optically active (R)-1-(3,5-bis(trifluoromethyl)phenyl)ethylamine N-monoethyl, represented by the following formula, are shown as follows.

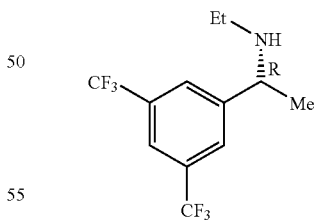

$^1$H-NMR (TMS, CDCl$_3$), δppm: 1.09 (t, 7.2 Hz, 3H), 1.37 (d, 6.4 Hz, 3H), 1.40 (br, 1H), 2.36-2.49 (m, 1H), 2.49-2.63 (m, 1H), 3.92 (q, 6.4 Hz, 1H), 7.75 (Ar—H, 1H), 7.81 (Ar—H, 2H).

In chiral gas chromatography, the major enantiomer peaks of Example 14 were identical with the minor enantiomer peaks of Example 13, and the minor enantiomer peaks of Example 14 were identical with the major enantiomer peaks of Example 13.

EXAMPLE 15

SYNTHESIS OF OPTICALLY ACTIVE (S)-1-(3,5-BIS(TRIFLUOROMETHYL)PHENYL) PENTYLAMINE N-MONOMETHYL

Step (c), Dehydration and Condensation

At first, 6.56 g (22.00 mmol, 1 eq.) of 3,5-bis(trifluoromethyl)phenyl n-butyl ketone, 3.40 g (28.06 mmol, 1.28 eq.) of (S)-1-phenylethylamine, and 0.30 g (2.20 mmol, 0.10 eq.) of zinc chloride were added to 100 ml of toluene. The resulting mixture was stirred for 101 hr under a heated reflux condition, while water (by-product) was removed from a Dean-Stark trap. The resulting reaction liquid was washed with 5% sodium hydroxide aqueous solution and then 1.4N ammonium chloride aqueous solution. The recovered organic layer was dried with anhydrous sodium sulfate, filtrated, concentrated and vacuum-dried, thereby obtaining 8.89 g of a crude product of an optically active imine represented by the following formula.

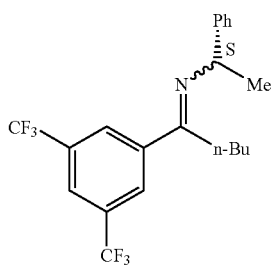

The conversion was found by gas chromatography to be 98%. The molecular ratio of E configuration to Z configuration of the crude product was found by $^1$H-NMR to be 85:15.

$^1$H-NMR (TMS; CDCl$_3$) of E configuration, δppm: 0.92 (t, 8.0 Hz, 3H), 1.28-1.50 (m, 4H), 1.55 (d, 6.7 Hz, 3H), 2.77 (t, 8.0 Hz, 2H), 4.91 (q, 6.7 Hz, 1H), 7.10-7.55 (Ar—H, 5H), 7.88 (Ar—H, 1H), 8.26 (Ar—H, 2H).

$^1$H-NMR (standard substance: TMS; solvent: CDCl$_3$) of Z configuration, δppm: 0.92 (t, 8.0 Hz, 3H), 1.28-1.50 (m, 4H), 1.55 (d, 6.7 Hz, 3H), 2.77 (t, 8.0 Hz, 2H), 4.17 (q, 6.7 Hz, 1H), 7.10-7.55 (Ar—H, 5H), 8.09 (Ar—H, 1H), 8.51 (Ar—H, 2H).

Step (d), Asymmetric Reduction

At first, 8.89 g (22.00 mmol, 1 eq.) of the crude product of the optically active imine produced by the above step (c) were added to 88 ml of methanol. The resulting solution was cooled down to −20° C. Then, 1.00 g (26.43 mmol, 1.20 eq.) of sodium borohydride were added, followed by stirring for 12 hr at from the same temperature to 0° C. After the reaction, 1N hydrochloric acid aqueous solution was added to decompose the remaining sodium borohydride. Then, the reaction liquid was made basic by adding 2N sodium hydroxide aqueous solution, followed by extraction with toluene. The collected organic layer was washed with saturated brine, dried with anhydrous sodium sulfate, filtrated, concentrated, and vacuum-dried, thereby obtaining 8.99 g of a crude product of an optically active secondary amine represented by the following formula.

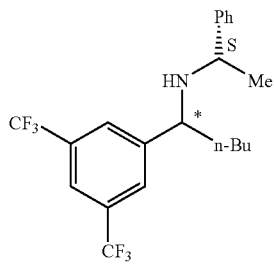

It was found by gas chromatography that conversion of the crude product was 100% and that the ratio of a diastereomer of S—S configuration to a diastereomer of R—S configuration was 85:15.

$^1$H-NMR (TMS, CDCl$_3$) of S—S configuration, δppm: 0.82 (t, 7.0 Hz, 3H), 0.95-1.15 (m, 1H), 1.10-1.32 (m, 3H), 1.28 (d, 8.0 Hz, 3H), 1.40-1.85 (m, 2H), 1.68 (br, 1H), 3.35 (q, 8.0 Hz, 1H), 3.44 (t, 7.0 Hz, 1H), 7.13 (Ar—H, 2H), 7.26 (Ar—H, 1H), 7.33 (Ar—H, 2H), 7.66 (Ar—H, 2H), 7.77 (Ar—H, 1H).

$^1$H-NMR (TMS, CDCl$_3$) of R—S configuration, δppm: 0.86 (t, 7.0 Hz, 3H), 0.95-1.15 (m, 1H), 1.10-1.32 (m, 3H), 1.37 (d, 8.0 Hz, 3H), 1.40-1.85 (m, 2H), 1.68 (br, 1H), 3.68 (q, 8.0 Hz, 1H), 3.74 (t, 7.0 Hz, 1H), 7.17 (Ar—H, 2H), 7.25 (Ar—H, 1H), 7.33 (Ar—H, 2H), 7.61 (Ar—H, 2H), 7.63 (Ar—H, 1H).

Step (a), Alkylation

At first, 1.10 g (2.69 mmol, 1 eq.) of the above crude product of the optically active secondary amine, 3.00 g (21.14 mmol, 7.86 eq.) of methyl iodide, and 0.75 g (5.43 mmol, 2.02 eq.) of anhydrous potassium carbonate were added to 5.0 ml of dimethylformamide, followed by stirring at room temperature for 43 hr. After the reaction, the reaction liquid was diluted with ethyl acetate, followed by washing with water and saturated brine, drying with anhydrous sodium sulfate, filtration, concentration, and vacuum drying, thereby obtaining 1.99 g of a crude product of an optically active tertiary amine represented by the following formula.

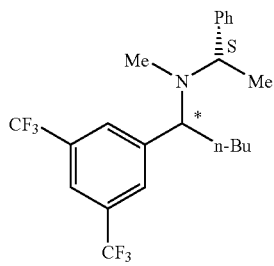

Conversion was found by gas chromatography to be 95%. Furthermore, the crude product was purified by a silica gel column chromatography (ethyl acetate:n-hexane=1:50), thereby obtaining 0.89 g of a purified product of the optically active tertiary amine. The yield was 79%.

$^1$H-NMR (TMS, CDCl$_3$) of S—S configuration, δppm: 0.84 (t, 7.2 Hz, 3H), 0.93-1.13 (m, 1H), 1.13-1.35 (m, 3H), 1.28 (d, 6.8 Hz, 3H), 1.59-1.78 (m, 1H), 1.82-2.00 (m, 1H), 2.13 (s, 3H), 3.47 (q, 6.8 Hz, 1H), 3.73 (t, 7.3 Hz, 1H), 7.21-7.42 (Ar—H, 5H), 7.61 (Ar—H, 2H), 7.77 (Ar—H, 1H).

¹H-NMR (TMS, CDCl₃) of R—S configuration, δppm: 0.85 (t, 7.3 Hz, 3H), 0.93-1.13 (m, 1H), 1.13-1.35 (m, 3H), 1.32 (d, 6.8 Hz, 3H), 1.59-1.78 (m, 1H), 1.82-2.00 (m, 1H), 2.12 (s, 3H), 3.66 (q, 6.8 Hz, 1H), 3.76 (t, 7.3 Hz, 1H), 7.21-7.42 (Ar—H, 5H), 7.61 (Ar—H, 2H), 7.76 (Ar—H, 1H).

Step (b), Hydrogenolysis

To 1.4 ml of methanol, 0.57 g (1.37 mmol, 1 eq.) of the above purified product of the optically active tertiary amine and 10.0 mg (0.04 wt % Pd) of a palladium catalyst (having 5% palladium carried on an activated carbon containing 50 wt % of water) were added. The hydrogen pressure was adjusted to 0.5 MPa, and the stirring was conducted at 60° C. for 14 hr. After the reaction, the reaction liquid was filtrated using a filtration aid (CELITE (trade name)), concentrated, and vacuum-dried, thereby obtaining 0.42 g of a crude product of an optically active (S)-1-(3,5-bis(trifluoromethyl)phenyl)pentylamine N-monomethyl, represented by the following formula.

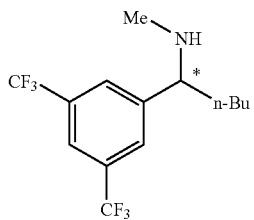

The yield was 98%. The above crude product was found by chiral gas chromatography to have a conversion of 100% and an enantiomeric excess of 70% ee. In terms of severing position selectivity whether the N—C* bond is severed at the broken line "a" to produce a compound A or at the broken line "b" to produce a compound B (i.e., the above optically active (S)-1-(3,5-bis(trifluoromethyl)phenyl)pentylamine N-monomethyl) in the above formula 11, the above crude product was found by chiral gas chromatography to contain 1 part by mole of the compound A and 99 parts by mole of the compound B.

¹H-NMR (TMS, CDCl₃), δppm: 0.86 (t, 7.2 Hz, 3H), 1.04-1.18 (m, 1H), 1.18-1.37 (m, 3H), 1.55-1.68 (m, 1H), 1.68-1.82 (m, 1H), 2.26 (s, 3H), 2.60 (br, 1H), 3.60 (t, 7.2 Hz, 1H), 7.76 (Ar—H, 2H), 7.78 (Ar—H, 1H).

EXAMPLE 16

SYNTHESIS OF OPTICALLY ACTIVE (R)-1-(3,5-BIS(TRIFLUOROMETHYL)PHENYL)PENTYLAMINE N-MONOMETHYL

Example 15 was repeated except in that (S)-1-phenylethylamine was replaced in the step (c) with (R)-1-phenylethylamine, thereby obtaining an optically active (R)-1-(3, 5-bis(trifluoromethyl)phenyl)pentylamine N-monomethyl.

NMR data of an optically active tertiary amine, represented by the following formula, are shown as follows.

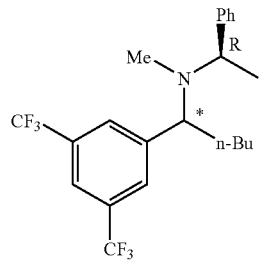

¹H-NMR (TMS, CDCl₃) of R—R configuration, δppm: 0.84 (t, 7.2 Hz, 3H), 0.93-1.13 (m, 1H), 1.13-1.35 (m, 3H), 1.28 (d, 6.8 Hz, 3H), 1.59-1.78 (m, 1H), 1.82-2.00 (m, 1H), 2.13 (s, 3H), 3.47 (q, 6.8 Hz, 1H), 3.73 (t, 7.3 Hz, 1H), 7.21-7.42 (Ar—H, 5H), 7.61 (Ar—H, 2H), 7.77 (Ar—H, 1H).

¹H-NMR (TMS, CDCl₃) of S—R configuration, δppm: 0.85 (t, 7.3 Hz, 3H), 0.93-1.13 (m, 1H), 1.13-1.35 (m, 3H), 1.32 (d, 6.8 Hz, 3H), 1.59-1.78 (m, 1H), 1.82-2.00 (m, 1H), 2.12 (s, 3H), 3.66 (q, 6.8 Hz, 1H), 3.76 (t, 7.3 Hz, 1H), 7.21-7.42 (Ar—H, 5H), 7.61 (Ar—H, 2H), 7.76 (Ar—H, 1H).

NMR data of an optically active (R)-1-(3,5-bis(trifluoromethyl)phenyl)pentylamine N-monomethyl, represented by the following formula, are shown as follows.

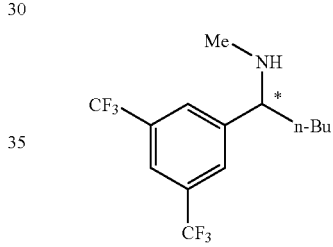

¹H-NMR (TMS, CDCl₃), δppm: 0.86 (t, 7.2 Hz, 3H), 1.04-1.18 (m, 1H), 1.18-1.37 (m, 3H), 1.55-1.68 (m, 1H), 1.68-1.82 (m, 1H), 2.26 (s, 3H), 2.60 (br, 1H), 3.60 (t, 7.2 Hz, 1H), 7.76 (Ar—H, 2H), 7.78 (Ar—H, 1H).

In chiral gas chromatography, the major enantiomer peaks of Example 16 were identical with the minor enantiomer peaks of Example 15, and the minor enantiomer peaks of Example 16 were identical with the major enantiomer peaks of Example 15.

EXAMPLE 17

SYNTHESIS OF OPTICALLY ACTIVE (S)-1-(4-TRIFLUOROMETHOXYPHENYL) ETHYLAMINE N-MONOMETHYL

Step (c), Dehydration and Condensation

At first, 5.00 g (24.49 mmol, 1 eq.) of 4-trifluoromethoxyphenyl methyl ketone, 3.26 g (26.90 mmol, 1.10 eq.) of (S)-1-phenylethylamine, and 0.23 g (1.69 mmol, 0.07 eq.) of zinc chloride were added to 24.5 ml of toluene. The resulting mixture was stirred for 22 hr under a heated reflux condition, while water (by-product) was removed from a Dean-Stark trap. The resulting reaction liquid was washed with 1.5% sodium hydroxide aqueous solution and then 1.5N ammonium chloride aqueous solution. The recovered organic layer was concentrated and vacuum-dried, thereby obtaining 7.61 g of a crude product of an optically active imine represented by the following formula.

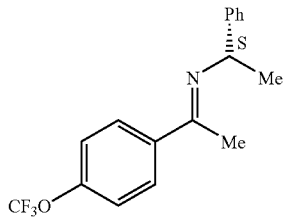

The conversion was found by gas chromatography to be 96%.

¹H-NMR (TMS; CDCl₃), δppm: 1.53 (d, 6.8 Hz, 3H), 2.27 (s, 3H), 4.83 (q, 6.8 Hz, 1H), 7.22 (Ar—H, 2H), 7.23 (Ar—H, 1H), 7.33 (Ar—H, 2H), 7.45 (Ar—H, 2H), 7.88 (Ar—H, 2H).

Step (d), Asymmetric Reduction

At first, 7.61 g (24.49 mmol, 1 eq.) of the crude product of the optically active imine produced by the above step (c) were added to 18.7 ml of methanol. The resulting solution was cooled down to −5° C. Then, 0.93 g (24.58 mmol, 1.00 eq.) of sodium borohydride were added, followed by stirring for 2 hr at the same temperature. After the reaction, 1N hydrochloric acid aqueous solution was added to decompose the remaining sodium borohydride. Then, the reaction liquid was made basic by adding 3N sodium hydroxide aqueous solution, followed by extraction with toluene. The collected organic layer was washed with saturated brine, dried with anhydrous sodium sulfate, filtrated, concentrated, and vacuum-dried, thereby obtaining 7.66 g of a crude product of an optically active secondary amine represented by the following formula.

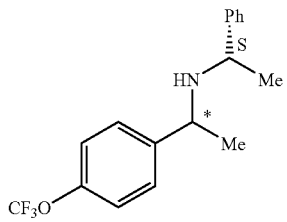

It was found by gas chromatography that conversion of the crude product was 100% and that the ratio of a diastereomer of S—S configuration to a diastereomer of R—S configuration was 85:15.

¹H-NMR (TMS, CDCl₃) of S—S configuration, δppm: 1.24 (d, 6.8 Hz, 3H), 1.27 (d, 6.8 Hz, 3H), 1.55 (br, 1H), 3.46 (q, 6.8 Hz, 1H), 3.52 (q, 6.8 Hz, 1H), 7.09-7.37 (Ar—H, 9H).

¹H-NMR (TMS, CDCl₃) of R—S configuration, δppm: 1.33 (d, 6.4 Hz, 3H), 1.35 (d, 6.4 Hz, 3H), 1.55 (br, 1H), 3.76 (q, 6.4 Hz, 2H), 7.09-7.37 (Ar—H, 9H)

Step (a), Alkylation

At first, 3.50 g (11.19 mmol, 1 eq.) of the above crude product of the optically active secondary amine, 2.49 g (22.61 mmol, 2.02 eq.) of methyl methanesulfonate, and 2.42 g (22.59 mmol, 2.02 eq.) of 2,6-lutidine were added to a mixed solution of 1.0 ml of dimethylformamide and 10.2 ml of tetrahydrofuran, followed by stirring at 60° C. for 16 hr. After the reaction, the reaction liquid was filtrated using a filtration aid (CELITE (trade name)), followed by dilution with toluene, washing with saturated sodium hydrogencarbonate and saturated brine, drying with anhydrous sodium sulfate, filtration, concentration, and vacuum drying, thereby obtaining 3.93 g of a crude product of an optically active tertiary amine represented by the following formula.

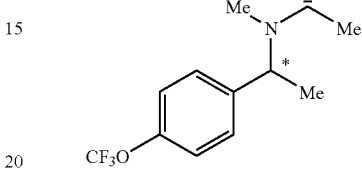

Conversion was found by gas chromatography to be 95%. Furthermore, the crude product was purified by a silica gel column chromatography (ethyl acetate:n-hexane=1:20), thereby obtaining 3.04 g of a purified product of the optically active tertiary amine. The total yield from the dehydration and the condensation to the alkylation was 84%.

¹H-NMR (TMS, CDCl₃) of S—S configuration, δppm: 1.32 (d, 6.8 Hz, 3H), 1.34 (d, 6.8 Hz, 3H), 1.98 (s, 3H), 3.80 (q, 6.8 Hz, 1H), 3.85 (q, 6.8 Hz, 1H), 7.10-7.46 (Ar—H, 9H).

Step (b), Hydrogenolysis

To 3.0 ml of methanol, 0.97 g (3.00 mmol, 1 eq.) of the above purified product of the optically active tertiary amine, 0.90 g (14.99 mmol, 5.00 eq.) of acetic acid and 48.5 mg (0.125 wt % Pd) of a palladium catalyst (having 5% palladium carried on an activated carbon containing 50 wt % of water) were added. The hydrogen pressure was adjusted to 0.5 MPa, and the stirring was conducted at 60° C. for 16 hr. After the reaction, the reaction liquid was filtrated using a filtration aid (CELITE (trade name)), concentrated, and vacuum-dried, thereby obtaining a crude product of an acetate of an optically active (S)-1-(4-trifluoromethoxyphenyl)ethylamine N-monomethyl, represented by the following formula.

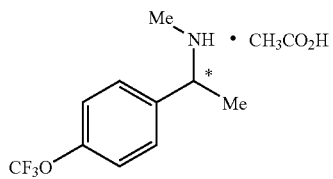

Then, 1N sodium hydroxide aqueous solution was added to the above crude product of the acetate to have a basic solution, followed by extraction with ethyl acetate. The recovered organic layer was dried with anhydrous sodium sulfate, followed by filtration, concentration and vacuum drying, thereby obtaining 0.59 g of a crude product of an optically active (S)-1-(4-trifluoromethoxyphenyl)ethylamine N-monomethyl, represented by the following formula.

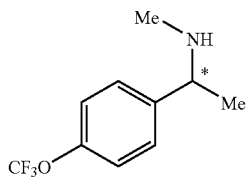

The yield was 89%. The above crude product was found by chiral gas chromatography to have a conversion of 100% and an enantiomeric excess of 70% ee. In terms of severing position selectivity whether the N—C* bond is severed at the broken line "a" to produce a compound A or at the broken line "b" to produce a compound B (i.e., the above optically active (S)-1-(4-trifluoromethoxyphenyl)ethylamine N-monomethyl) in the above formula 11, the above crude product was found by chiral gas chromatography to contain 1 part by mole of the compound A and 99 parts by mole of the compound B.

$^1$H-NMR (TMS, CDCl$_3$), δppm: 1.34 (d, 6.8 Hz, 3H), 1.63 (br, 1H), 2.30 (s, 3H), 3.67 (q, 6.8 Hz, 1H), 7.17 (Ar—H, 2H), 7.33 (Ar—H, 2H).

EXAMPLE 18

SYNTHESIS OF OPTICALLY ACTIVE (R)-1-(4-TRIFLUOROMETHOXYPHENYL) ETHYLAMINE N-MONOMETHYL

Example 17 was repeated except in that (S)-1-phenylethylamine was replaced in the step (c) with (R)-1-phenylethylamine, thereby obtaining an optically active (R)-1-(4-trifluoromethoxyphenyl)ethylamine N-monomethyl.

NMR data of an optically active tertiary amine, represented by the following formula, are shown as follows.

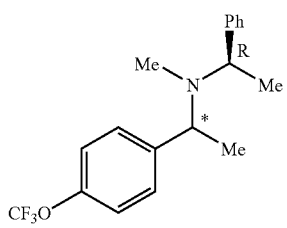

$^1$H-NMR (TMS, CDCl$_3$) of R—R configuration, δppm: 1.32 (d, 6.8 Hz, 3H), 1.34 (d, 6.8 Hz, 3H), 1.98 (s, 3H), 3.80 (q, 6.8 Hz, 1H), 3.85 (q, 6.8 Hz, 1H), 7.10-7.46 (Ar—H, 9H).

NMR data of an optically active (R)-1-(4-trifluoromethoxyphenyl)ethylamine N-monomethyl, represented by the following formula, are shown as follows.

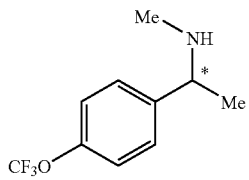

$^1$H-NMR (TMS, CDCl$_3$), δppm: 1.34 (d, 6.8 Hz, 3H), 1.63 (br, 1H), 2.30 (s, 3H), 3.67 (q, 6.8 Hz, 1H), 7.17 (Ar—H, 2H), 7.33 (Ar—H, 2H).

In chiral gas chromatography, the major enantiomer peaks of Example 18 were identical with the minor enantiomer peaks of Example 17, and the minor enantiomer peaks of Example 18 were identical with the major enantiomer peaks of Example 17.

The entire contents of Japanese Patent Application No. 2002-261148 (filed Sep. 6, 2002), which is a basic Japanese application of the present application, are incorporated herein by reference.

What is claimed is:

1. An optically active tertiary amine represented by the formula 3,

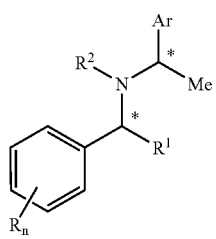

[3]

wherein

R represents a fluorine atom, trifluoromethyl group or trifluoromethoxy group, n represents an integer of from 1 to 5, each of $R^1$ and $R^2$ independently represents an alkyl group having a carbon atom number of from 1 to 6, Me represents a methyl group, Ar represents a phenyl group or 1- or 2-naphthyl group, and

* represents a chiral carbon.

2. An optically active tertiary amine according to claim 1, which is represented by the following formula,

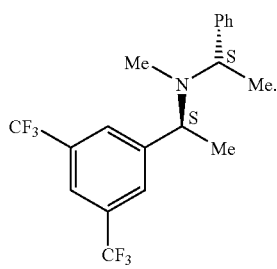

3. An optically active tertiary amine according to claim 1, which is represented by the following formula,

4. An optically active tertiary amine according to claim 1, which is represented by the following formula,

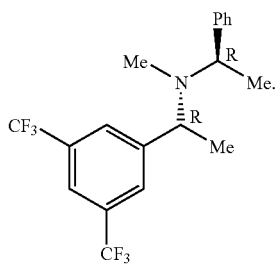

5. An optically active tertiary amine according to claim 1, which is represented by the following formula,

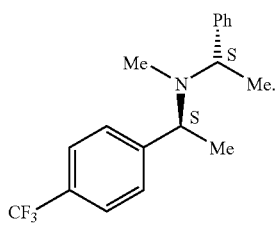

6. An optically active tertiary amine according to claim 1, which is represented by the following formula,

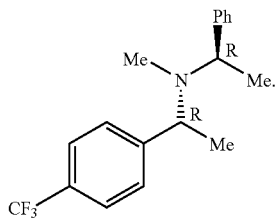

7. An optically active tertiary amine according to claim 1, which is represented by the following formula,

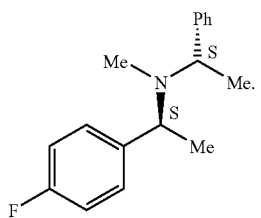

8. An optically active tertiary amine according to claim 1, which is represented by the following formula,

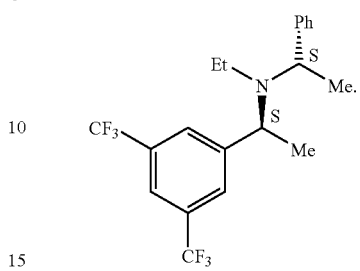

9. An optically active tertiary amine according to claim 1, which is represented by the following formula,

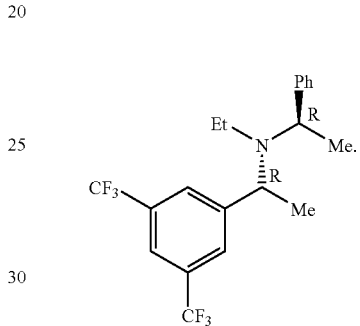

10. An optically active tertiary amine according to claim 1, which is represented by the following formula,

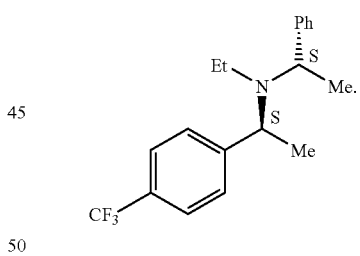

11. An optically active tertiary amine according to claim 1, which is represented by the following formula,

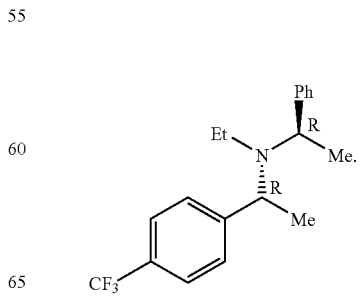

12. An optically active tertiary amine according to claim 1, which is represented by the following formula,
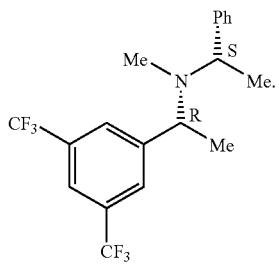
13. An optically active tertiary amine according to claim 1, which is represented by the following formula,
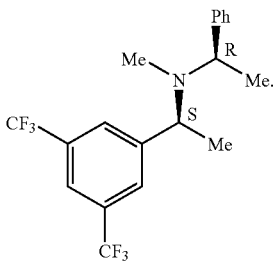
* * * * *